(12) United States Patent
Weinert et al.

(10) Patent No.: US 7,941,200 B2
(45) Date of Patent: May 10, 2011

(54) SYSTEM AND METHOD FOR DETERMINING DRUG ADMINISTRATION INFORMATION

(75) Inventors: Stefhan Weinert, Pendleton, IN (US); Paul Galley, Cumberland, IN (US); Ajay Thukral, Indianapolis, IN (US); Siva Chittajallu, Indianapolis, IN (US); Harvey Buck, Indianapolis, IN (US); Robin Wagner, Fishers, IN (US); Kym Marco, Indianapolis, IN (US); James R. Long, Fishers, IN (US); Steven Bousamra, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1345 days.

(21) Appl. No.: 11/297,733

(22) Filed: Dec. 8, 2005

(65) Prior Publication Data
US 2007/0179434 A1 Aug. 2, 2007

(51) Int. Cl.
*A61B 5/00* (2006.01)

(52) U.S. Cl. .......... 600/347; 600/345; 600/365; 604/67; 702/19

(58) Field of Classification Search .................. 600/365, 600/345–347; 604/65–67; 702/19
See application file for complete search history.

(56) References Cited

U.S. PATENT DOCUMENTS

| | | | |
|---|---|---|---|
| 4,475,901 A | 10/1984 | Kraegen et al. | |
| 4,731,726 A | 3/1988 | Allen, III | |
| 5,019,974 A | 5/1991 | Beckers | |
| 5,233,520 A | 8/1993 | Kretsch et al. | |
| 5,412,560 A | 5/1995 | Dennision | |
| 5,997,475 A | 12/1999 | Bortz | |
| 6,352,505 B1 * | 3/2002 | Bortz | 600/300 |
| 6,379,301 B1 | 4/2002 | Worthington et al. | |
| 6,544,212 B2 | 4/2003 | Galley et al. | |
| 6,554,798 B1 * | 4/2003 | Mann et al. | 604/131 |
| 6,572,542 B1 | 6/2003 | Houben et al. | |
| 6,602,191 B2 | 8/2003 | Quy | |
| 6,740,075 B2 | 5/2004 | Lebel et al. | |
| 6,810,290 B2 | 10/2004 | Lebel et al. | |
| 6,835,175 B1 | 12/2004 | Porumbescu | |
| 6,931,327 B2 | 8/2005 | Goode, Jr. et al. | |
| 7,137,951 B2 * | 11/2006 | Pilarski | 600/300 |
| 2001/0005830 A1 | 6/2001 | Kuroyanagi | |
| 2001/0037060 A1 | 11/2001 | Thompson et al. | |
| 2002/0015723 A1 | 2/2002 | Koenig | |

(Continued)

FOREIGN PATENT DOCUMENTS

EP 1 522 920 A2 9/2004

(Continued)

OTHER PUBLICATIONS

Animas ezManager User Manual, Copyright Animas Corporation 2005.

(Continued)

*Primary Examiner* — Charles A Marmor, II
*Assistant Examiner* — Michael D'Angelo
(74) *Attorney, Agent, or Firm* — Dinsmore & Shohl, LLP

(57) ABSTRACT

A system for determining drug administration information may comprise an input device providing for user input of feed forward information having a first parameter component and a second parameter component, a data storage device and a processor. The data storage device may have stored therein a map correlating values of the first and second parameters to drug administration information. The processor may be responsive to user input of the feed forward information to determine corresponding drug administration information according to the map.

20 Claims, 22 Drawing Sheets

U.S. PATENT DOCUMENTS

| | | |
|---|---|---|
| 2002/0019707 A1 | 2/2002 | Cohen et al. |
| 2002/0022774 A1 | 2/2002 | Karnieli |
| 2002/0156351 A1 | 10/2002 | Sagel |
| 2003/0004756 A1 | 1/2003 | Okamoto et al. |
| 2003/0028089 A1 | 2/2003 | Galley et al. |
| 2003/0032867 A1 | 2/2003 | Crothall et al. |
| 2003/0040821 A1 | 2/2003 | Case |
| 2003/0046401 A1 | 3/2003 | Abbott et al. |
| 2003/0114836 A1 | 6/2003 | Estes et al. |
| 2003/0182160 A1 | 9/2003 | Lahteenmaki |
| 2003/0187683 A1 | 10/2003 | Kirchhoff et al. |
| 2003/0208110 A1* | 11/2003 | Mault et al. .................. 600/300 |
| 2003/0208113 A1* | 11/2003 | Mault et al. .................. 600/316 |
| 2003/0225731 A1 | 12/2003 | Vidgen |
| 2003/0226695 A1 | 12/2003 | Mault |
| 2004/0015102 A1* | 1/2004 | Cummings et al. ........... 600/584 |
| 2004/0107116 A1 | 6/2004 | Brown |
| 2004/0116780 A1 | 6/2004 | Brown |
| 2004/0162702 A1 | 8/2004 | Pandipati et al. |
| 2004/0167464 A1 | 8/2004 | Ireland et al. |
| 2004/0171925 A1 | 9/2004 | Kirchhoff et al. |
| 2004/0176666 A1 | 9/2004 | Chait |
| 2004/0180810 A1 | 9/2004 | Pilarski |
| 2004/0204955 A1 | 10/2004 | Kirchhoff et al. |
| 2004/0210456 A1 | 10/2004 | Kirchhoff et al. |
| 2004/0225533 A1 | 11/2004 | Cosentino et al. |
| 2004/0243443 A1 | 12/2004 | Asano et al. |
| 2004/0267098 A1 | 12/2004 | Moore |
| 2005/0010416 A1 | 1/2005 | Anderson et al. |
| 2007/0060869 A1 | 3/2007 | Tolle et al. |
| 2007/0060870 A1 | 3/2007 | Tolle et al. |

FOREIGN PATENT DOCUMENTS

| | | |
|---|---|---|
| EP | 1759726 A2 | 3/2007 |
| WO | 99/66394 | 12/1999 |
| WO | 02/100266 A1 | 12/2002 |
| WO | 2005/037092 A1 | 4/2005 |
| WO | 2005081170 A2 | 9/2005 |

OTHER PUBLICATIONS

Deltec Cozmo User Manual, Copyright Smith Medical family of companies 2004.

Paradigm 512 & 712 Insulin Pumps User Guide, Copyright Medtronic MiniMed 2005.

Accu-Chek Advisor User Manual, Copyright Roche Diagnostics 2005.

* cited by examiner

| BG (mg/dl) | MEAL CAT (B,L,D,S) | EIC (gr) | EMED (min) | AMD | RMD | AMS | RMS | AMSF | AMSC | AMSP | TGI | MCB (I.U.) | CB (I.U.) | ... | OTHER | ... | DATE | TIME |
|---|---|---|---|---|---|---|---|---|---|---|---|---|---|---|---|---|---|---|
| 140 | L | 60 | 90 | M | N | M | N | M | M | M | 55 | 9.2 | 1.6 | ... | | ... | 9/1/05 | 12:00 |
| 130 | D | 80 | 90 | MF | SN | ML | LN | L | ML | L | 70 | 9.8 | 1.8 | ... | | ... | 9/1/05 | 17:30 |
| 105 | B | 45 | 75 | M | SSN | S | SN | MS | M | S | 45 | 7.6 | 0 | ... | ... | ... | 9/2/05 | 8:15 |
| ... | ... | ... | ... | ... | ... | ... | ... | ... | ... | ... | ... | ... | ... | ... | ... | ... | ... | ... |

FIG. 13

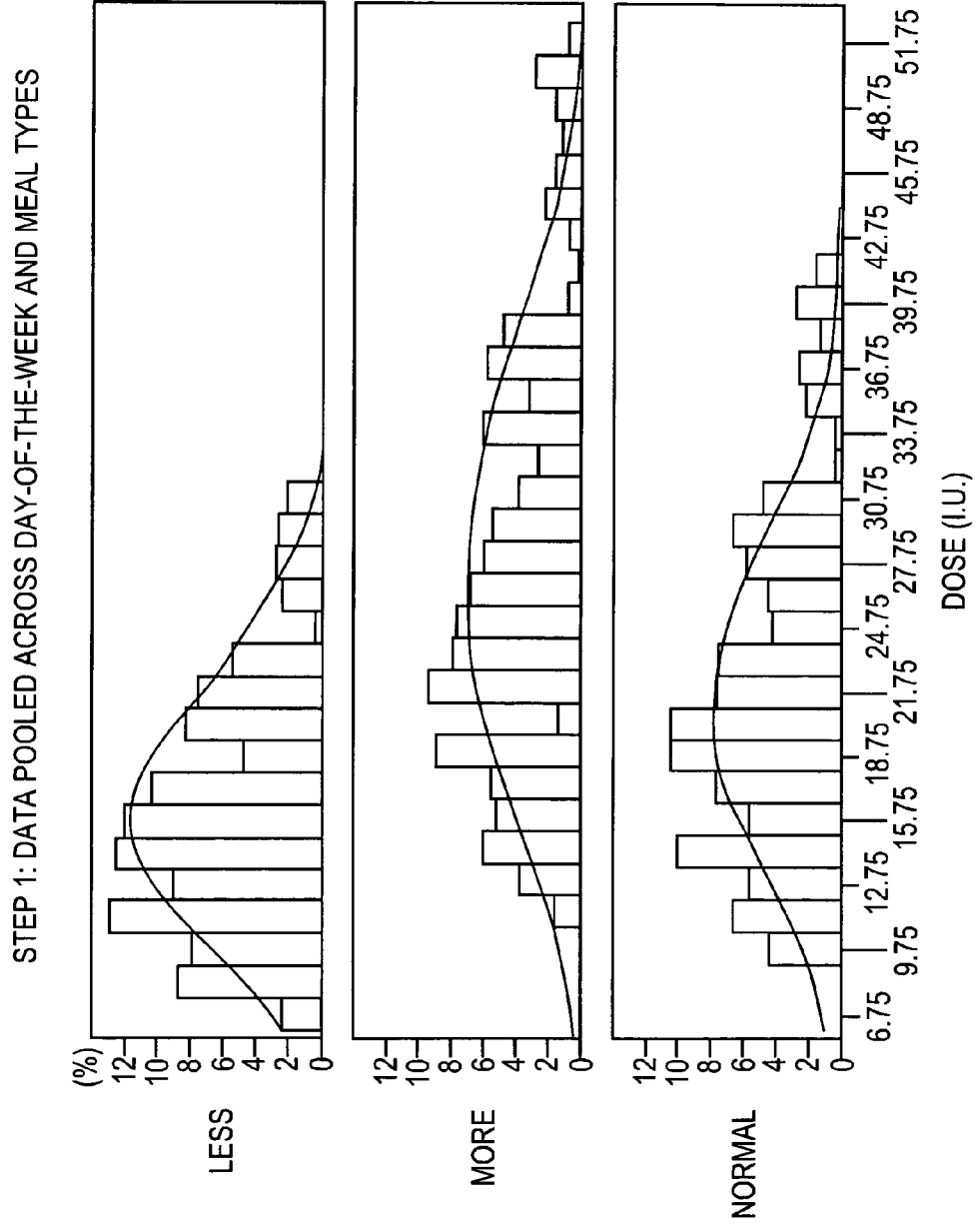

SYSTEM AND METHOD FOR DETERMINING DRUG ADMINISTRATION INFORMATION

FIELD OF THE INVENTION

The present invention relates generally to techniques for determining drug administration information, and more specifically to systems for determining insulin administration information based on a user input of user-related feed forward information.

BACKGROUND

A number of diabetes control arrangements exist that are configured to recommend or automatically administer insulin boluses of various types, of various quantities and/or at various intervals, based on some amount of feed forward information provided by the user. It is desirable to simplify the content, and minimize the amount, of such feed forward information required to be supplied by the user in determining such bolus information.

SUMMARY

The present invention may comprise one or more of the features recited in the attached claims, and/or one or more of the following features and combinations thereof. A system for determining drug administration information may comprise an input device providing for user input of feed forward information having a first parameter component and a second parameter component, a data storage device and a processor. The data storage device may have stored therein a map correlating values of the first and second parameters to drug administration information. The processor may be responsive to user input of the feed forward information to determine corresponding drug administration information according to the map.

The system may further include a display unit. The processor may be configured to display at least some of the corresponding drug administration information on the display unit. The processor may be configured to control the display unit to display a graphical user interface having a first axis defined by values of the first parameter and a second axis defined by values of the second parameter. The graphical user interface may provide for the user input of feed forward information in the form of a single user selection of a corresponding pair of the first and second parameter values.

The graphical user interface may include a touch responsive interface providing for the single user selection of a corresponding pair of the first and second parameter values.

The graphical user interface may define a grid-type user interface providing for single user selection of discrete pairs of the first and second parameter values. Alternatively, the graphical user interface may define a continuous function of the first and second parameter values.

The drug may be a blood glucose lowering drug. The drug may be, for example, insulin. The input device may be configured to provide for user input of feed forward information in the form of meal information having the first parameter component corresponding to carbohydrate content of the meal and the second parameter component corresponding to an expected speed of overall glucose absorption from the meal by the user. The input device may include a display unit, and the processor may be configured to control the display unit to display a graphical user interface having a first axis defined by values of the carbohydrate content and a second axis defined by values of the expected speed of overall glucose absorption from the meal by the user. The graphical user interface may provide for the user input of feed forward information in the form of a single user selection of a corresponding pair of the carbohydrate content and expected speed values.

The processor may be configured to control the display unit to display the carbohydrate content values in the form of direct estimates of carbohydrate weight. Alternatively, the processor may be configured to control the display unit to display the carbohydrate content values in the form of meal size values. Alternatively still, the processor may be configured to control the display unit to display the carbohydrate content values in the form of meal size values relative to a reference meal size.

The processor may be configured to control the display unit to display the expected speed values in the form of meal duration values. Alternatively, the processor may be configured to control the display unit to display the expected speed values in the form of meal duration values relative to a reference meal duration. Alternatively still, the processor may be configured to control the display unit to display the expected speed values in the form of total glycemic index values.

The processor may be configured to control the display unit to display a graphical user interface having a first axis defined by values of the carbohydrate content and a second axis defined by values of the expected speed of overall glucose absorption from the meal by the user. The graphical user interface may provide for the user input of feed forward information in the form of user selection of corresponding pairs of the carbohydrate content and expected speed values. The processor may be configured to control the display unit to display the values of the expected speed in the form of a fat amount, a protein amount and a carbohydrate amount, and to display the values of the carbohydrate content in the form of meal size values for each of the fat amount, protein amount and carbohydrate amount. The graphical user interface may provide for the user input of feed forward information in the form of user selection a meal size value in terms of fat amount, a meal size in terms of protein amount and a meal size in terms of carbohydrate amount. Alternatively, the processor may be configured to control the display unit to display the meal size values in the form of fat amount, protein amount and carbohydrate amount relative to reference meal size values in terms of fat, protein and carbohydrate amounts respectively.

The input device may be configured to provide for user input of additional feed forward information in the form of exercise information. In such cases, the data storage device may have stored therein an additional map correlating the exercise information to modification information, and the processor may be responsive to user input of the exercise information to modify the corresponding drug administration information according to the modification information determined via the additional map.

The input device may be configured to provide for user input of additional feed forward information in the form of user stress information. In such cases, the data storage device may have stored therein an additional map correlating the user stress information to modification information, and the processor may be responsive to user input of the user stress information to modify the corresponding drug administration information according to the modification information determined via the additional map.

The input device may be configured to provide for user input of additional feed forward information in the form of user illness information. In such cases, the data storage device may have stored therein an additional map correlating the user illness information to modification information, and the processor may be responsive to user input of the user illness information to modify the corresponding drug administration information according to the modification information determined via the additional map.

The input device may be configured to provide for user input of additional feed forward information in the form of user menstrual cycle information. In such cases, the data storage device may have stored therein an additional map correlating the user menstrual cycle information to modification information, and the processor may be responsive to user input of the user menstrual cycle information to modify the corresponding drug administration information according to the modification information determined via the additional map.

The processor may be configured to monitor occurrences of user acceptance and rejection of the drug administration information determined according to the map, and to determine whether the system is acceptable for use by the user based at least in part on the occurrences of user acceptance and rejection of the drug administration information. If the processor determines that the system is acceptable for use by the user, the processor may be configured to then determine whether the system requires recalibration based at least in part on the occurrences of user acceptance and rejection of the drug administration information.

The system may further comprise means for providing for input of user feedback information. The processor may be configured to monitor the user feedback information and determine whether the system is acceptable for use by the user based at least in part on the user feedback information. If the processor determines that the system is acceptable for use by the user, the processor may be configured to then determine whether the system requires recalibration based at least in part on the user feedback information.

The system may further comprise means for providing for input of health care professional feedback information. The processor may be configured to monitor the health care professional feedback information and determine whether the system is acceptable for use by the user based at least in part on the health care professional feedback information. If the processor determines that the system is acceptable for use by the user, the processor may be configured to then determine whether the system requires recalibration based at least in part on the health care professional feedback information.

The system may further comprise at least one model-based function responsive to measurement of one or more user conditions to estimate another user condition different than the one or more user conditions. The processor may be configured to monitor the at least one model-based function and determine whether the system is acceptable for use by the user based at least in part on the at least one model-based function. If the processor determines that the system is acceptable for use by the user, the processor may be configured to then determine whether the system requires recalibration based at least in part on the at least one model-based function.

A method of determining drug administration information may comprise receiving a single user input of feed forward information, wherein the feed forward information includes user specified values of a first parameter and a second parameter. The method may further include correlating the first and second parameters to drug administration information.

The method may further include displaying at least some of the drug administration information on a display unit.

Correlating the first and second parameters to drug administration information may include processing the first and second parameters using a map configured to map values of the first parameter and values of the second parameter to corresponding drug administration information.

Receiving the single user input of feed forward information the input device may include receiving the single user input of feed forward information via a graphical user interface, wherein the graphical user interface may have a first axis defined by values of the first parameter and a second axis defined by values of the second parameter.

The drug may be a blood glucose lowering drug. The drug may be, for example, insulin. The first parameter may correspond to carbohydrate content of a meal and the second parameter may correspond to an expected speed of overall glucose absorption from the meal by the user.

The values of the first parameter may be displayed on the graphical user interface in the form of carbohydrate weight. Alternatively, the values of the first parameter may be displayed on the graphical user interface in the form of meal size values. Alternatively still, the values of the first parameter may be displayed on the graphical user interface in the form of meal size values relative to a reference meal size.

The values of the second parameter may be displayed on the graphical user interface in the form of meal duration values. Alternatively, the values of the second parameter may be displayed on the graphical user interface in the form of meal duration values relative to a reference meal duration. Alternatively still, the values of the second parameter may be displayed on the graphical user interface in the form of total glycemic index values.

The values of the second parameter component may be displayed on the graphical user interface in the form of a fat amount, a protein amount and a carbohydrate amount. The values of the first parameter component may be displayed on the graphical user interface in the form of meal size values for each of the fat amount, the protein amount and the carbohydrate amount. The values of the first parameter may be displayed on the graphical user interface in the form of meal size values for each of the fat amount, the protein amount and the carbohydrate amount values relative to reference meal size values for each of the fat amount, the protein amount and the carbohydrate amount respectively.

In embodiments wherein the first parameter corresponds to carbohydrate content of the meal and the second parameter corresponds to an expected speed of overall glucose absorption from the meal by the user, the method may further include receiving a single user input of additional feed forward information including user exercise information, and modifying the drug administration information according to the user exercise information. Alternatively or additionally, the method may further include receiving a single user input of additional feed forward information including user stress information, and modifying the drug administration information according to the user stress information. Alternatively or additionally still, the method may further include receiving a single user input of additional feed forward information including user illness information, and modifying the drug administration information according to the user illness information. Alternatively or additionally still, the method may further include receiving a single user input of additional feed forward information including user menstrual cycle information, and modifying the drug administration information according to the user menstrual cycle information.

The method may further comprise monitoring occurrences of user acceptance and rejection of the drug administration information determined according to the map, and determining whether the method is acceptable for use by the user based at least in part on the occurrences of user acceptance and rejection of the drug administration information. The method may further comprise the following if the method is acceptable for use by the user; determining whether recalibration of the method is required based at least in part on the occurrences of user acceptance and rejection of the drug administration information.

The method may alternatively or additionally comprise monitoring user feedback information that is different than the feed forward information, and determining whether the method is acceptable for use by the user based at least in part on the user feedback information. The method may further comprise the following if the method is acceptable for use by the user; determining whether recalibration of the method is required based at least in part on the user feedback information.

The method may alternatively or additionally comprise monitoring health care professional feedback information, and determining whether the method is acceptable for use by the user based at least in part on the health care professional feedback information. The method may further comprise the following if the method is acceptable for use by the user; determining whether recalibration of the method is required based at least in part on the health care professional feedback information.

The method may alternatively or additionally comprise defining at least one model-based function responsive to measurement of one or more user conditions to estimate another user condition different than the one or more user conditions, and determining whether the method is acceptable for use by the user based at least in part on the at least one model-based function. The method may further comprise the following if the method is acceptable for use by the user; determining whether recalibration of the method is required based at least in part on the at least one model-based function.

A method may be provided for determining patient suitability for a graphical user interface configured to allow the patient to select feed forward information from which drug administration information is determined. The method may comprise collecting patient-relevant information relating to events that are defined any of a number of categories of feed forward information and corresponding drug administration information. The method may further comprise processing the collected patient-relevant information to determine whether one or more regular patterns in the patient-relevant information can be identified that allow acceptable prediction of appropriate values of the drug administration information based on corresponding categories of the feed forward information. If the one or more regular patterns in the patient-relevant information can be identified, the method may further comprise processing the collected patient-relevant information to determine whether the number of categories of feed forward information can be reduced. If the number of categories of feed forward information can be reduced, the method may further comprise reducing the number of categories of feed forward information.

Processing the collected patient-relevant information to determine whether one or more regular patterns in the patient-relevant information can be identified may comprise sorting the patient-relevant information according to at least one variable of the patient-relevant information and pooling the patient-relevant information over all remaining variables of the patient-relevant information. Processing the collected patient-relevant information to determine whether one or more regular patterns in the patient-relevant information can be identified may further comprise calculating a coefficient of variation for the patient-relevant information relating to the at least one variable. Processing the collected patient-relevant information to determined whether one or more regular patterns in the patient-relevant information can be identified may further comprise determining that the patient-relevant information sorted by the at least one variable allows acceptable prediction of appropriate values of the drug administration information based on corresponding categories of the feed forward information if the coefficient of variation for the patient-relevant information relating to the at least one variable does not exceed a maximum coefficient of variation. Processing the collected patient-relevant information to determine whether one or more regular patterns in the patient-relevant information can be identified may further comprise executing the following steps if the coefficient of variation for the patient-relevant information relating to the at least one variable exceeds a maximum coefficient of variation sorting the patient-relevant information according to at least one variable of the patient-relevant information and according to at least another variable of the patient-relevant information, and pooling the patient-relevant information over all remaining variables of the patient-relevant information, calculating coefficients of variation for the patient-relevant information relating to the at least one variable and to the at least another variable, and determining that the patient-relevant information sorted by the at least one variable and by the at least another variable allows acceptable prediction of appropriate values of the drug administration information based on corresponding categories of the feed forward information if the coefficient of variations for the patient-relevant information relating to the at least one variable and to the at least another variable do not exceed a maximum coefficient of variation. Processing the collected patient-relevant information to determine whether one or more regular patterns in the patient-relevant information can be identified may further comprise executing the following step if either of the coefficients of variation for the patient-relevant information relating to the at least one variable and to the at least another variable exceed the maximum coefficient of variation executing the sorting, calculating and determining steps using an iteratively finer pooling of the patient-relevant information until none of the corresponding number of coefficients of variation exceed the maximum coefficient of variation.

Processing the collected patient-relevant information to determine whether the number of categories of feed forward information can be reduced may comprise determining merging scenarios for all of the number of categories of feed forward information. Processing the collected patient-relevant information to determine whether the number of categories of feed forward information can be reduced may further comprise analyzing each of the merging scenarios to determine whether feed forward categories can be merged according to that merging scenario. Processing the collected patient-relevant information to determine whether the number of categories of feed forward information can be reduced may further comprise selecting a best merging scenario from each of the merging scenarios that have feed forward categories that can be merged. Processing the collected patient-relevant information to determine whether the number of categories of feed forward information can be reduced may further comprise merging feed forward categories according to the best merging scenario. Processing the collected patient-relevant information to determine whether the number of categories of feed forward information can be reduced may comprise executing the determining, analyzing, selecting and merging steps for each of the one or more regular patterns in the patient-relevant information.

The method may further comprise pre-screening the patient to determine whether the patient is an acceptable candidate for the graphical user interface. The method may further include executing the collecting step, the two processing steps and the reducing step only if the patient is an acceptable candidate for the graphical user interface.

The method may further comprise creating a map that maps the patient-selectable categories of the feed forward information to corresponding drug administration information, and implementing the map with the graphical user interface.

The method may further comprise monitoring occurrences of user acceptance and rejection of the drug administration information determined according to the map, and determining whether the graphical user interface is acceptable for use by the user based at least in part on the occurrences of user acceptance and rejection of the drug administration information. The method may further comprise the following if the graphical user interface is acceptable for use by the user; determining whether the graphical user interface requires recalibration based at least in part on the occurrences of user acceptance and rejection of the drug administration information.

The method may alternatively or additionally comprise monitoring user feedback information that is different than the feed forward information, and determining whether the graphical user interface is acceptable for use by the user based at least in part on the user feedback information. The method may further comprise the following if the graphical user interface is acceptable for use by the user; determining whether the graphical user interface requires recalibration based at least in part on the user feedback information.

The method may alternatively or additionally comprise monitoring health care professional feedback information, and determining whether the graphical user interface is acceptable for use by the user based at least in part on the health care professional feedback information. The method may further comprise the following if the graphical user interface is acceptable for use by the user; determining whether the graphical user interface requires recalibration based at least in part on the health care professional feedback information.

The method may alternatively or additionally comprise defining at least one model-based function responsive to measurement of one or more user conditions to estimate another user condition different than the one or more user conditions, and determining whether the graphical user interface is acceptable for use by the user based at least in part on the at least one model-based function. The method may further comprise the following if the graphical user interface is acceptable for use by the user; determining whether the graphical user interface requires recalibration based at least in part on the at least one model-based function.

The events defined by the feed forward information may be meals ingested by the patient, and the drug may be a blood glucose lowering drug. The events defined by the feed forward information may further include exercise undertaken by the patient. Alternatively or additionally, the events defined by the feed forward information may further include stress experienced by the patient. Alternatively or additionally, the events defined by the feed forward information may further include illness experienced by the patient. Alternatively or additionally, the events defined by the feed forward information may further include the patient's menstrual cycle.

The events defined by the feed forward information may be exercise events undertaken by the patient, and the drug may be a blood glucose lowering drug.

The events defined by the feed forward information may be stress events experienced by the patient, and the drug may be a blood glucose lowering drug.

The events defined by the feed forward information may be illness events experienced by the patient, and the drug may be a blood glucose lowering drug.

The events defined by the feed forward information may be menstrual events experienced by the patient, and the drug may be a blood glucose lowering drug.

BRIEF DESCRIPTION OF THE DRAWINGS

FIG. 4 illustrates a further embodiment of a graphical user interface for entering meal-related information into the system of FIG. 1.

FIG. 5 illustrates yet another embodiment of a graphical user interface for entering meal-related information into the system of FIG. 1.

FIG. 13 is a table illustrating one embodiment of patient log for collecting patient-relevant information according to the process illustrated in FIGS. 10-12.

FIGS. 14A-14K are example plots of some patient-relevant information vs. insulin bolus amount grouped in various ways according one embodiment of the statistical analyses step of the process of FIG. 10.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same. It will be understood that throughout this document, the terms "user" and "patient" are used interchangeably.

Figure 1:
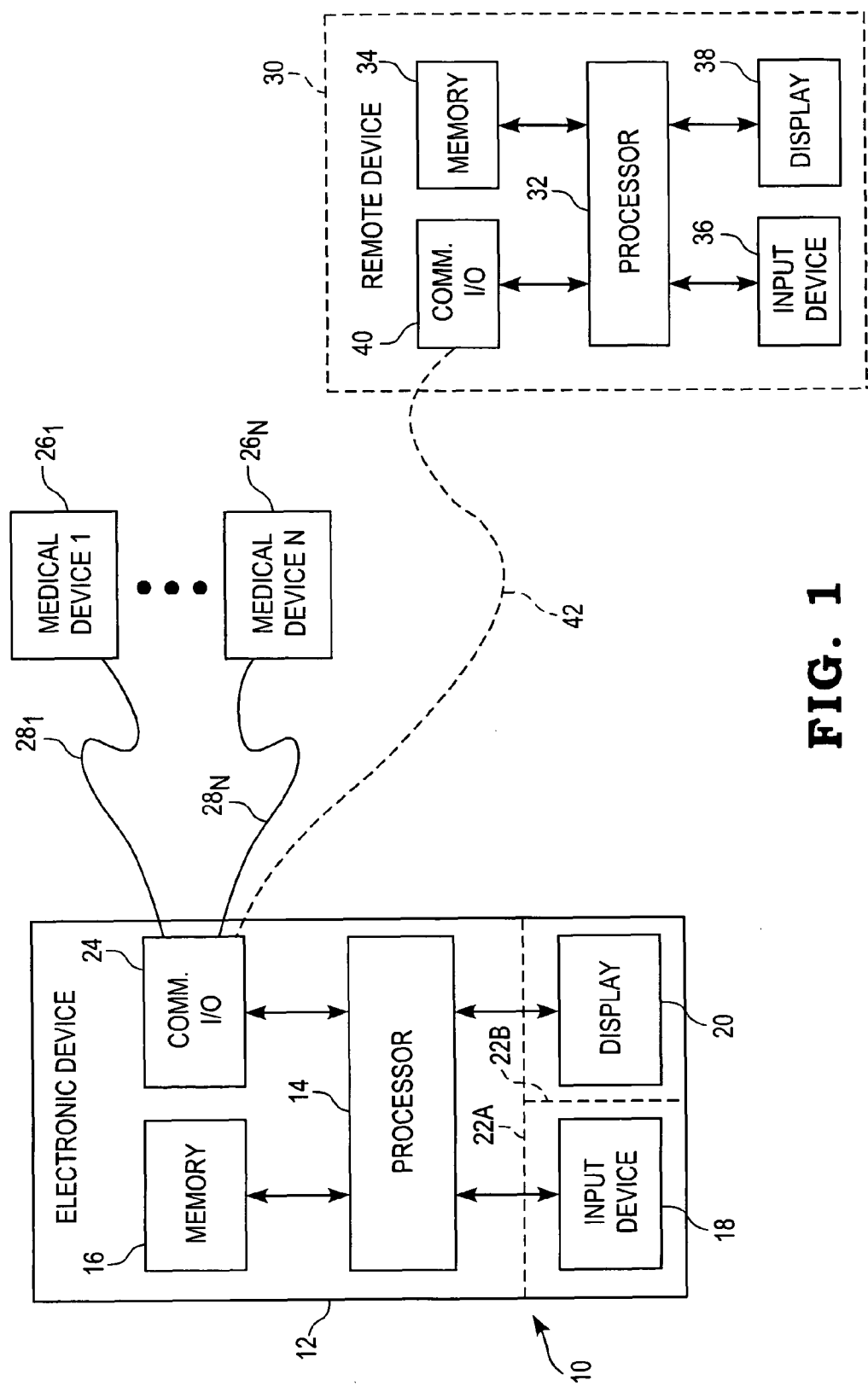
FIG. 1 is a block diagram of one illustrative embodiment of a system for determining drug administration information.

Referring now to FIG. 1, a block diagram of one illustrative embodiment of a system 10 for determining drug administration information is shown. In the illustrated embodiment, the system 10 includes an electronic device 12 having a processor 14 in data communication with a memory unit 16, an input device 18, a display 20 and a communication input/output unit 24. The electronic device 12 may be provided in the form of a general purpose computer, central server, personal computer (PC), lap top or notebook computer, personal data assistant (PDA) or other hand-held device, external infusion pump, blood glucose meter, analyte sensing system, or the like. The electronic device 12 may be configured to operate in accordance with one or more conventional operating systems including for example, but not limited to, windows, linux and Mac OS and embedded OS such as QNX, eCOS, WinCE and palm OS, and may be configured to process data according to one or more conventional internet protocols for example, but not limited to, NetBios, TCP/IP and AppleTalk. In any case, the electronic device 12 forms part of a fully closed-loop, semi closed-loop or open-loop diabetes control system, examples of which will be described hereinafter. The processor 14 is, in the illustrated embodiment, microprocessor-based, although the processor 14 may alternatively formed of one or more general purpose and/or application specific circuits and operable as described hereinafter. The memory unit 16 includes, in the illustrated embodiment, sufficient capacity to store data, one or more software algorithms executable by the processor 14 and other data. The memory unit 16 may include one or more conventional memory or other data storage devices.

The input device 18 may be used in a conventional manner to input and/or modify data. In the illustrated embodiment, the display 20 is also included for viewing information relating to operation of the device 12 and/or system 10. Such a display may be a conventional display device including for example, but not limited to, a light emitting diode (LED) display, a liquid crystal display (LCD), a cathode ray tube (CRT) display, or the like. Alternatively or additionally, the display 20 may be or include an audible display configured to communicate information to a user, another person or another electronic system having audio recognition capabilities via one or more coded patterns, vibrations, synthesized voice responses, or the like. Alternatively or additionally, the display 20 may be or include one or more tactile indicators configured to display tactile information that may be discerned by the user or another person.

In one embodiment, the input device 18 may be or include a conventional keyboard or key pad for entering alphanumeric data into the processor 14. Such a keyboard or key pad may include one or more keys or buttons configured with one or more tactile indicators to allow users with poor eyesight to find and select an appropriate one or more of the keys, and/or to allow users to find and select an appropriate one or more of the keys in poor lighting conditions. Alternatively or additionally, the input device 18 may be or include a conventional mouse or other conventional point and click device for selecting information presented on the display 20. Alternatively or additionally, the input device 18 may include the display 20 configured as a graphical user interface (GUI). In this embodiment, the display 20 may include one or more selectable inputs that a user may select by touching an appropriate portion of the display 20 using an appropriate implement. Alternatively or additionally, the input device 18 may include a number of switches or buttons that may be activated by a user to select corresponding operational features of the device 12 and/or system 10. Alternatively or additionally, the input device 18 may be or include voice activated circuitry responsive to voice commands to provide corresponding input data to the processor 14. In any case, the input device 18 and/or display 20 may be included with or separate from the electronic device 12 as indicated by the dashed lines 22A and 22B.

In some embodiments, the system 10 may include a number, N, of medical devices $26_1$-$26_N$, wherein N may be any positive integer. In such embodiments, any of the one or more medical devices $26_1$-$26_N$ may be implanted within the user's body, coupled externally to the user's body (e.g., such as an infusion pump), or separate from the user's body. Alternatively or additionally, one or more of the medical devices $26_1$-$26_N$ may be mounted to and/or form part of the electronic device 12. In the illustrated embodiment, the number of medical devices $26_1$-$26_N$ are each configured to communicate wirelessly with the communication I/O unit 24 of the electronic device 12 via one of a corresponding number of wireless communication links $28_1$-$28_N$. The wireless communications may be one-way or two-way. The form of wireless communication used may include, but should not be limited to, radio frequency (RF) communication, infrared (IR) communication, WiFi, RFID (inductive coupling) communication, acoustic communication, capacitive signaling (through a conductive body), galvanic signaling (through a conductive body), or the like. In any such case, the electronic device 12 and each of the number of medical devices $26_1$-$26_N$ include conventional circuitry for conducting such wireless communications circuit. Alternatively or additionally, one or more of the medical devices $26_1$-$26_N$ may be configured to communicate with the electronic device 12 via one or more conventional serial or parallel configured hardwire connections therebetween. Each of the one or more medical devices $26_1$-$26_N$ may include any one or more of a conventional processing unit, conventional input/output circuitry and/or devices and one or more suitable data and/or program storage devices.

In some embodiments, the system 10 may alternatively or additionally include a remote device 30, as illustrated in phantom in FIG. 1. The remote device 30 may include a conventional processor 32, which may be identical or similar to the processor 14, a conventional memory or other data storage unit 34, a conventional input device 36, which may be or include any one or more of the input devices described hereinabove with respect to the input device 18, a conventional display unit 38, which may be or include any one or more of the display units described hereinabove with respect to the display unit 20, and conventional communication I/O circuitry 40. The remote device 30 may be configured to communicate with the electronic device 12 via any conventional wired or wireless communication interface 42, which may be or include any of the communication interfaces or links described hereinabove.

The system 10 illustrated in FIG. 1 is, or forms part of, a conventional fully closed-loop, semi closed-loop or open-loop diabetes control arrangement. In this regard, the system 10 requires user input of some amount of feed forward information from which the system 10 determines, at least in part, insulin bolus administration information. Such insulin bolus administration information may be or include, for example, insulin bolus quantity or quantities, bolus type (e.g., normal or fast-acting, e.g., Regular, Lispro, etc.), insulin bolus delivery time, times or intervals (e.g., single delivery, multiple discrete deliveries, continuous delivery, etc.), and the like. Examples of user supplied feed forward information may be or include, for example but not limited to, user blood glucose concentration, information relating to a meal or snack that has been ingested, is being ingested, or is to be ingested sometime in the future, user exercise information, user stress information, user illness information, information relating to the user's menstrual cycle, and the like. In any case, the system 10 includes a delivery mechanism for delivering controlled amounts of a drug; e.g., insulin, glucagon, incretin, or the like, and/or offering an alternatively actionable therapy recommendation to the user via the display 20, e.g., ingesting carbohydrates, exercising, etc. The system 10 may be provided in any of a variety of conventional configurations, and examples of some such configurations will now be described. It will be understood, however, that the following examples are provided merely for illustrative purposes, and should not be considered limiting in any way. Those skilled in the art may recognize other possible implementations of a fully closed-loop, semi closed-loop or open-loop diabetes control arrangement, and any such other implementations are contemplated by this disclosure.

In a first example implementation of the system 10, the electronic device 12 is provided in the form of a conventional insulin pump configured to be worn externally to the user's body and also configured to controllably deliver insulin to the user's body. In this example, the number of medical devices $26_1$-$26_N$ may include one or more implanted sensors and/or sensor techniques for providing information relating to the physiological condition of the user. Examples of such implanted sensors may include, but should not be limited to, a glucose sensor, a body temperature sensor, a blood pressure sensor, a heart rate sensor, one or more bio-markers configured to capture one or more physiological states of the body, e.g., HBA1C, or the like. In implementations that include an implanted glucose sensor, the system 10 may be a fully closed-loop system operable in a conventional manner to automatically monitor blood glucose and deliver insulin, as appropriate, to maintain blood glucose at desired levels. The number of medical devices $26_1$-$26_N$ may alternatively or additionally include one or more sensors or sensing systems that are external to the user's body and/or sensor techniques for providing information relating to the physiological condition of the user. Examples of such sensors or sensing systems may include, but should not be limited to, a glucose strip sensor/meter, a body temperature sensor, a blood pressure sensor, a heart rate sensor, one or more bio-markers configured to capture one or more physiological states of the body, e.g., HBA1C, or the like. In implementations that include an external glucose sensor, the system 10 may be a closed-loop, semi closed-loop or open-loop system operable in a conventional manner to deliver insulin, as appropriate, based on glucose information provided thereto by the user. Information provided by any such sensors and/or sensor techniques may be communicated to the system 10 using any one or more conventional wired or wireless communication techniques. In this example implementation, the remote device 30 may also be included in the form of a handheld or otherwise portable electronic device configured to communicate information to and/or from the electronic device 12.

In a second example implementation of the system 10, the electronic device 12 is provided in the form of a handheld remote device, such as a PDA or other handheld device. In this example, the number of medical devices $26_1$-$26_N$ include at least one conventional implantable or externally worn drug pump. In one embodiment of this example, an insulin pump is configured to controllably deliver insulin to the user's body. In this embodiment, the insulin pump is configured to wirelessly transmit information relating to insulin delivery to the handheld device 12. The handheld device 12 is configured to monitor insulin delivery by the pump, and may further be configured to determine and recommend insulin bolus amounts, carbohydrate intake, exercise, and the like. The system 10 may or may not be configured in this embodiment to provide for transmission of wireless information from the handheld device 12 to the insulin pump.

In an alternate embodiment of this example, the handheld device 12 is configured to control insulin delivery to the user by determining insulin delivery commands and transmitting such commands to the insulin pump. The insulin pump, in turn, is configured to receive the insulin delivery commands from the handheld device 12, and to deliver insulin to the user according to the commands. The insulin pump, in this embodiment, may or may not further process the insulin pump commands provided by the handheld unit 12. In any case, the system 10 will typically be configured in this embodiment to provide for transmission of wireless information from the insulin pump back to the handheld device 12 to thereby allow for monitoring of pump operation. In either embodiment of this example, the system 10 may further include one or more implanted and/or external sensors of the type described in the previous example. In this example implementation, the remote device 30 may also be included in the form of, for example, a PC, PDA, laptop or notebook computer configured to communicate information to and/or from the electronic device 12.

Those skilled in the art will recognize other possible implementations of a fully closed-loop, semi closed-loop or open-loop diabetes control arrangement using at least some of the components of the system 10 illustrated in FIG. 1. For example, the electronic device 12 in one or more of the above examples may be provided in the form of a PDA, laptop, notebook or personal computer configured to communicate with one or more of the medical devices $26_1$-$26_N$, at least one of which is an insulin delivery system, to monitor and/or control the delivery of insulin to the user. As another example, the remote device 30 may be configured to communicate with the electronic device 12 and/or one or more of the medical devices $26_1$-$26_N$, to control and/or monitor insulin delivery to the patient, and/or to transfer one or more software programs and/or data to the electronic device 12. The remote device 30 may reside in a caregiver's office or other remote location, and communication between the remote device and any component of the system 10 may be accomplished via an intranet, internet (e.g., world-wide-web), cellular, telephone modem, RF, or other communication link. Any one or more conventional internet protocols may be used in such communications. Alternatively or additionally, any conventional mobile content delivery system; e.g., Wi-Fi, WiMAX, short message system (SMS), or other conventional message schema may be used to provide for communication between devices comprising the system 10. In any case, any such other implementations are contemplated by this disclosure.

Generally, the concentration of glucose in a person changes as a result of one or more external influences such as meals and exercise, and also changes resulting from various physiological mechanisms such as stress, illness, menstrual cycle and the like. In a person with diabetes, such changes can necessitate monitoring the person's blood glucose level and administering insulin or other blood glucose altering drug, e.g., glucose lowering or raising drug, as needed to maintain the person's blood glucose within desired ranges. In any of the above examples, the system 10 is thus configured to determine, based on some amount of patient-specific information, an appropriate amount, type and/or timing of insulin or other blood glucose altering drug to administer in order to maintain normal blood glucose levels without causing hypoglycemia or hyperglycemia. In some embodiments, the system 10 is configured in a conventional manner to control one or more external (e.g., subcutaneous, transcutaneous or transdermal) and/or implanted insulin pumps to automatically infuse or otherwise supply the appropriate amount and type of insulin to the user's body in the form of one or more insulin boluses. In other embodiments, the system 10 is configured in a conventional manner to display or otherwise notify the user of the appropriate amount, type and/or timing of insulin in the form of an insulin recommendation. In such embodiments, conventional hardware and/or software forming part of the system 10 allows the user to accept the recommended insulin amount, type and/or timing, or to reject it. If accepted, the system 10, in one embodiment, automatically infuses or otherwise provides the appropriate amount and type of insulin to the user's body in the form of one or more insulin boluses. If, on the other hand, the user rejects the insulin recommendation, conventional hardware and/or software forming part of the system 10 allows the user to override the system 10 and manually enter insulin bolus quantity, type, and/or timing. The system 10 is then configured in a conventional manner to automatically infuse or otherwise provide the user specified amount, type and/or timing of insulin to the user's body in the form of one or more insulin boluses. Alternatively, the appropriate amount and type of insulin corresponding to the insulin recommendation displayed by the system 10 may be manually injected into, or otherwise administered to, the patient's body. It will be understood, however, that the system 10 may alternatively or additionally be configured in like manner to determine, recommend and/or deliver other types of medication to a patient.

The system 10 is operable, as just described, to determine and either recommend or administer an appropriate amount of insulin or other blood glucose lowering drug to the patient in the form of one or more insulin boluses. In determining such appropriate amounts of insulin, the system 10 requires at least some information relating to one or more external influences and/or various physiological mechanisms associated with the patient. For example, if the patient is about to ingest, is ingesting, or has recently ingested, a meal or snack, the system 10 generally requires some information relating to the meal or snack to determine an appropriate amount, type and/or timing of one or more meal compensation boluses. When a person ingests food in the form of a meal or snack, the person's body reacts by absorbing glucose from the meal or snack over time. For purposes of this document, any ingesting of food may be referred to hereinafter as a "meal," and the term "meal" therefore encompasses traditional meals, e.g., breakfast, lunch and dinner, as well as intermediate snacks, drinks, etc.

The general shape of a glucose absorption profile for any person rises following ingestion of the meal, peaks at some measurable time following the meal, and then decreases thereafter. The speed i.e., the rate from beginning to completion, of any one glucose absorption profile typically varies for a person by meal composition, by meal type or time (e.g., breakfast, lunch, dinner or snack) and/or according to one or more other factors, and may also vary from day-to-day under otherwise identical meal circumstances. Generally, the feed forward information relating to such meal intake information supplied by the patient to the system 10 should contain, either explicitly or implicitly, an estimate of the carbohydrate content of the meal or snack, corresponding to the amount of carbohydrates that the patient is about to ingest, is ingesting, or has recently ingested, as well as an estimate of the speed of overall glucose absorption from the meal by the patient.

The estimate of the amount of carbohydrates that the patient is about to ingest, is ingesting, or has recently ingested, may be provided by the patient in any of various forms. Examples include, but are not limited to, a direct estimate of carbohydrate weight (e.g., in units of grams or other convenient weight measure), an amount of carbohydrates relative to a reference amount (e.g., dimensionless), an estimate of meal or snack size (e.g., dimensionless), and an estimate of meal or snack size relative to a reference meal or snack size (e.g., dimensionless). Other forms of providing for patient input of carbohydrate content of a meal or snack will occur to those skilled in the art, and any such other forms are contemplated by this disclosure.

The estimate of the speed of overall glucose absorption from the meal by the patient may likewise be provided by the patient in any of various forms. For example, for a specified value of the expected speed of overall glucose absorption, the glucose absorption profile captures the speed of the meal taken by the patient. As another example, the speed of overall glucose absorption from the meal by the patient also includes a time duration between ingesting of the meal by a person and the peak glucose absorption of the meal by that person, which captures the duration of the meal taken by the patient. The speed of overall glucose absorption may thus be expressed in the form of meal speed or duration. Examples of the expected speed of overall glucose absorption parameter in this case may include, but are not limited to, a compound parameter corresponding to an estimate of the meal speed or duration (e.g., units of time), a compound parameter corresponding to meal speed or duration relative to a reference meal speed or duration (e.g., dimensionless), or the like.

As another example of providing the estimate of the expected speed of overall glucose absorption parameter, the shape and duration of the glucose absorption profile may be mapped to the composition of the meal. Examples of the expected speed of overall glucose absorption parameter in this case may include, but are not limited to, an estimate of fat amount, protein amount and carbohydrate amount (e.g., in units of grams) in conjunction with a carbohydrate content estimate in the form of meal size or relative meal size, an estimate of fat amount, protein amount and carbohydrate amount relative to reference fat, protein and carbohydrate amounts in conjunction with a carbohydrate content estimate in the form of meal size or relative meal size, and an estimate of a total glycemic index of the meal or snack (e.g., dimensionless), wherein the term "total glycemic index" is defined for purposes of this document as a parameter that ranks meals and snacks by the speed at which the meals or snacks cause the person's blood sugar to rise. Thus, for example, a meal or snack having a low glycemic index produces a gradual rise in blood sugar whereas a meal or snack having a high glycemic index produces a fast rise in blood sugar. One exemplary measure of total glycemic index may be, but should not be limited to, the ratio of carbohydrates absorbed from the meal and a reference value, e.g., derived from pure sugar or white bread, over a specified time period, e.g., 2 hours. Other forms of providing for user input of the expected overall speed of glucose absorption from the meal by the patient, and/or for providing for user input of the expected shape and duration of the glucose absorption profile generally will occur to those skilled in the art, and any such other forms are contemplated by this disclosure.

The system 10 illustratively includes a graphic user interface providing for patient (user) input of meal related information having a first parameter component and a second parameter component. The graphic user interface is illustratively displayed on the display unit 20 of the electronic device 12, but may alternatively or additionally be displayed on the display unit 38 of the remote device 30. The processor 14 is configured to control the display unit 20 to display the graphic user interface on the electronic device 12 in a conventional manner. Alternatively or additionally, the processor 32 may be configured to control the display unit 38 to display the graphic user interface on the remote device 30 in a conventional manner. User input to the graphic user interface may be provided in any one or more conventional forms. Examples include, but are not limited to, one or more buttons or keys provided on the input device 18 and/or 36 of the corresponding device 12 and/or 30, a touch-sensitive screen of the display unit 20 and/or 38, one or more conventional point and click mechanisms, or the like.

Figure 2:
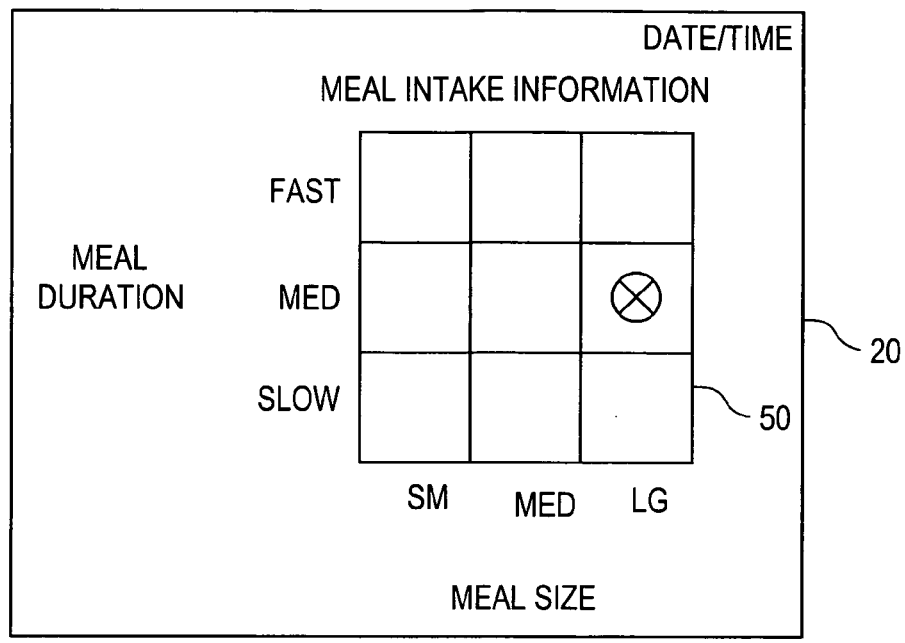
FIG. 2 illustrates one embodiment of a graphical user interface for entering meal-related information into the system of FIG. 1.

The first parameter component of the patient (user) input of meal related information illustratively corresponds to a carbohydrate amount or content of the meal that the patient is about to ingest, is ingesting, or has recently ingested, and the second parameter component illustratively corresponds to an expected speed of overall glucose absorption from the meal by the patient. Referring to FIG. 2, one exemplary embodiment of such a graphical user interface 50 providing for user input of meal intake information is shown. In the illustrated embodiment, the graphical user interface 50 is a grid-type user interface having one grid axis defined by carbohydrate content in the form of meal size and another grid axis defined by expected speed of overall glucose absorption from the meal by the patient in the form of meal duration. The meal size grid axis defines three different meal size or amount values in the form of "small", "medium" and "large" indicators, and the meal duration grid axis likewise defines three different meal duration values in the form of "slow", "medium" and "fast" indicators. The grid-type graphical user interface 50 provides for a single user selection of carbohydrate content and expected speed of overall glucose absorption information relating to the meal that the patient is about to ingest, is ingesting, or has recently ingested. As used herein, the phrase "single user selection" is defined as a single selection made by a user. It will be understood that the systems and methods described herein are not limited to a single user, and that rather the systems and methods described in this document may be implemented in a single or multiple user platform. In any case, the user has selected, in the illustrated example, a meal related input indicating that the meal that the patient is about to ingest, is ingesting, or has recently ingested is a large meal that will be, or that has been, ingested over a medium meal duration. In general, the terms "large," "medium," and "small" in this context are intended to encompass any conventional measure of meal size including for example, but not limited to, meal quantities or amounts using any specified units of weight, volume, etc.

Figure 3:
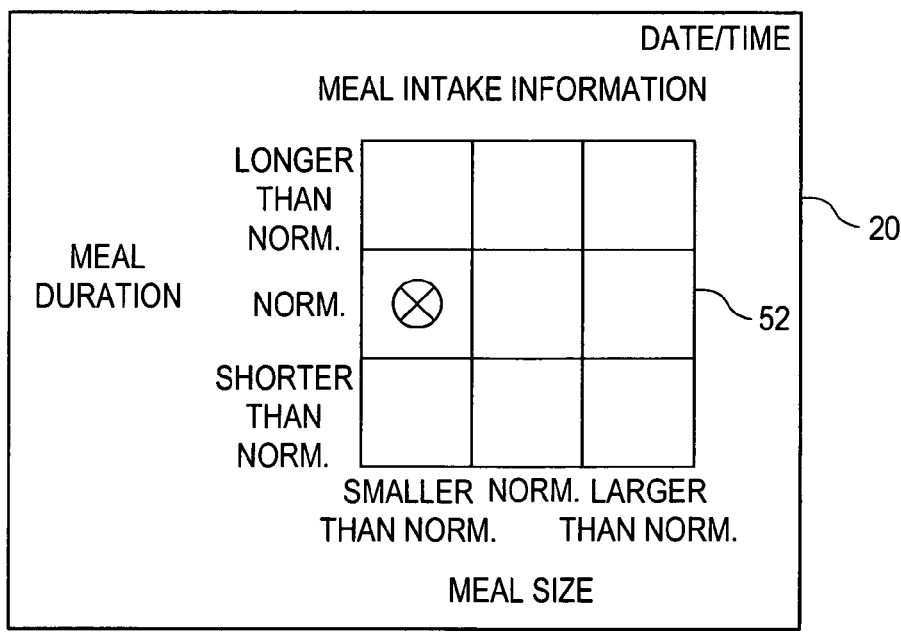
FIG. 3 illustrates another embodiment of a graphical user interface for entering meal-related information into the system of FIG. 1.

Referring to FIG. 3, another exemplary embodiment of a graphical user interface 52 providing for user input of meal intake information is shown. In the illustrated embodiment, the graphical user interface 52 is a grid-type user interface having one grid axis defined by carbohydrate content in the form of meal size relative to a reference meal size and another grid axis defined by expected speed of overall glucose absorption from the meal by the patient in the form of meal duration relative to a reference meal duration. The meal size grid axis defines three different meal size values in the form of "smaller than normal", "normal" and "larger than normal" indicators, and the meal duration grid axis likewise defines three different meal duration values in the form of "shorter than normal", "normal" and "longer than normal" indicators. The grid-type graphical user interface 52 provides for a single user selection of carbohydrate content and expected speed of overall glucose absorption information relating to the meal that the patient is about to ingest, is ingesting, or has recently ingested. In the illustrated example, the user has selected a meal related input indicating that the meal that the patient is about to ingest, is ingesting, or has recently ingested is a smaller than normal meal and that the meal duration is about the same as a normal meal duration. In general, the terms "larger" and "smaller" in this context are intended to encompass any conventional measure of meal size relative to a specified "normal" meal size including for example, but not limited to, meal quantities or amounts using any specified units of weight, volume, etc.

Figures 4, 5:
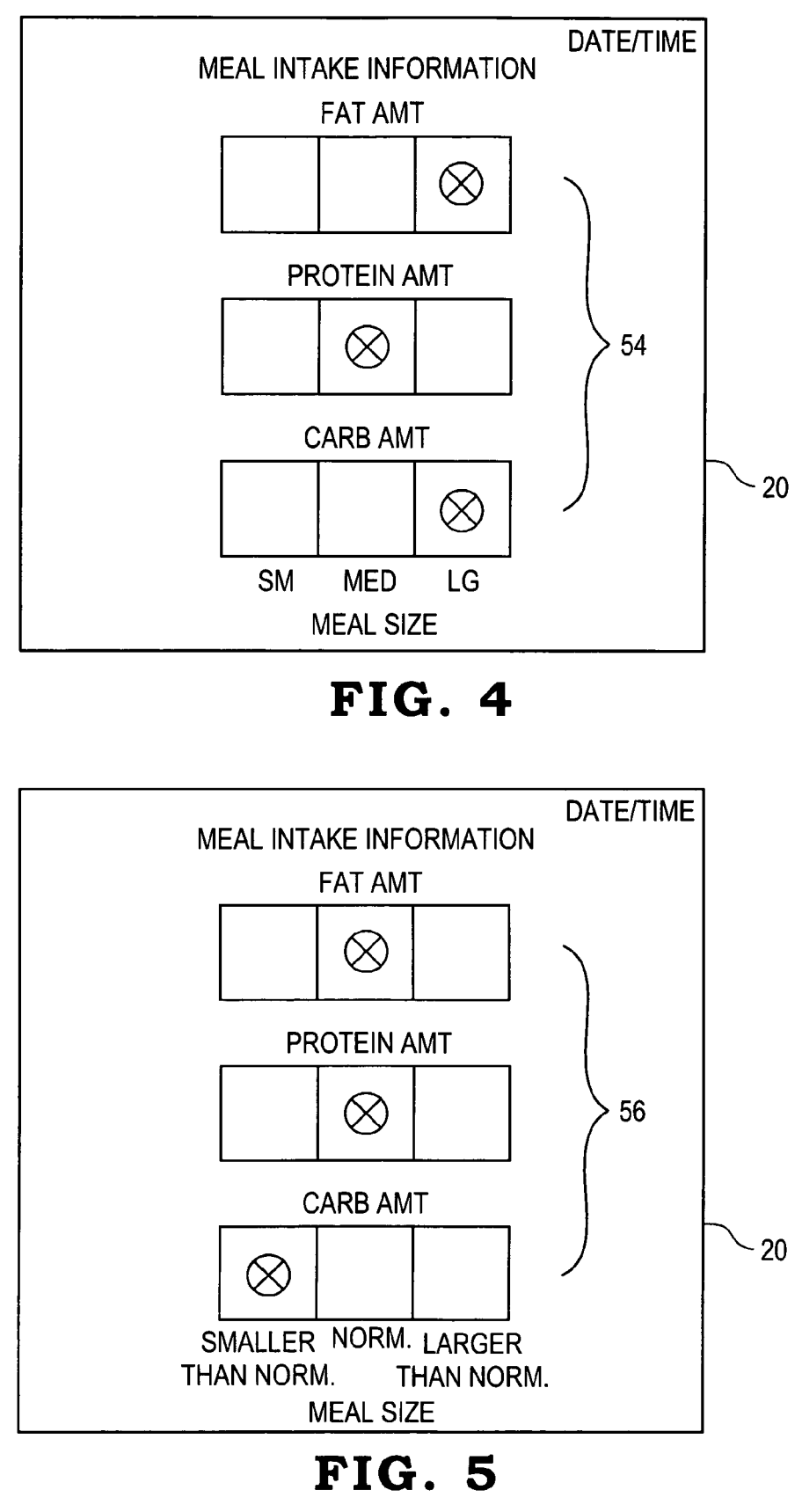

Referring to FIG. 4, yet another exemplary embodiment of a graphical user interface 54 providing for user input of meal intake information is shown. In the illustrated embodiment, the graphical user interface 54 is a grid-type user interface having one grid axis defined by carbohydrate content in the form of meal size and another grid axis defined by expected speed of overall glucose absorption in the form of fat amount, protein amount and carbohydrate amount of the meal. The graphical user interface 54 thus requires three separate selections to be input by the user, as compared with the single input associated with the embodiments illustrated and described with respect to FIGS. 1 and 2. The fat amount, protein amount and carbohydrate amount will be mapped, as described briefly hereinabove, to an expected speed of overall glucose absorption from the meal by the patient. The meal size grid axis defines three different meal size values in the form of "small", "medium" and "large" indicators. The grid-type graphical user interface 54 provides for the user selection of carbohydrate content and expected speed overall glucose absorption information relating to the meal that the patient is about to ingest, is ingesting, or has recently ingested. In the illustrated example, the user has selected a meal related input indicating that the meal that the patient is about to ingest, is ingesting, or has recently ingested has a large amount of fat, a medium amount of protein and a large amount of carbohydrates. In general, the terms "large," "medium," and "small" in this context are intended to encompass any conventional measure of meal size including for example, but not limited to, meal quantities or amounts using any specified units of weight, volume, etc.

Generally, any desired functional relationship may be used in the present embodiment to map the three meal composition amounts to corresponding meal speed or meal duration values. One exemplary functional relationship may be, but should not be limited to, assigning equal weights to the three meal composition components, computing percentages of the three user-specified meal composition values, assigning equally spaced thresholds to the two interfaces between the three meal size values, e.g., 33% and 66%, and then comparing the percentages of the three meal composition values to the threshold percentage values to determine meal speed. Using the example illustrated in FIG. 4, the small, medium and large components are assigned values of 1, 2 and 3 respectively. The percentage of fat is thus 3/8 or 37.5%, the percentage of protein is 2/8 or 25%, and the percentage of carbohydrates is 3/8 or 37.5%. The percentages of fat and carbohydrates are thus both medium, and the percentage of protein is small, resulting in a composite meal speed of medium to medium-slow.

Referring to FIG. 5, still another exemplary embodiment of a graphical user interface 56 providing for user input of meal intake information is shown. In the illustrated embodiment, the graphical user interface 56 is a grid-type user interface having one grid axis defined by carbohydrate content in the form of meal size relative to a reference meal size and another grid axis defined by expected speed of overall glucose absorption from the meal by the patient in the form of fat amount, protein amount and carbohydrate amount. As with the graphical user interface 54, the graphical user interface 56 thus requires three separate selections to be input by the user, as compared with the single input associated with the embodiments illustrated and described with respect to FIGS. 1 and 2. The user-specified fat, protein and carbohydrate amounts will be mapped to corresponding meal speed or meal duration values using any desired functional relationship therebetween as just described. The meal size grid axis defines three different meal size values in the form of "smaller than normal", "normal" and "larger than normal" indicators. The grid-type graphical user interface 56 provides for user selection of carbohydrate content and expected speed of glucose absorption information relating to the meal that the patient is about to ingest, is ingesting, or has recently ingested. In the illustrated example, the user has selected a meal related input indicating that the meal that the patient is about to ingest, is ingesting, or has recently ingested has a normal fat amount, a normal protein amount and a smaller than normal carbohydrate amount. In general, the terms "larger" and "smaller" in this context are intended to encompass any conventional measure of meal size relative to a specified "normal" meal size including for example, but not limited to, meal quantities or amounts using any specified units of weight, volume, etc.

Figure 6:
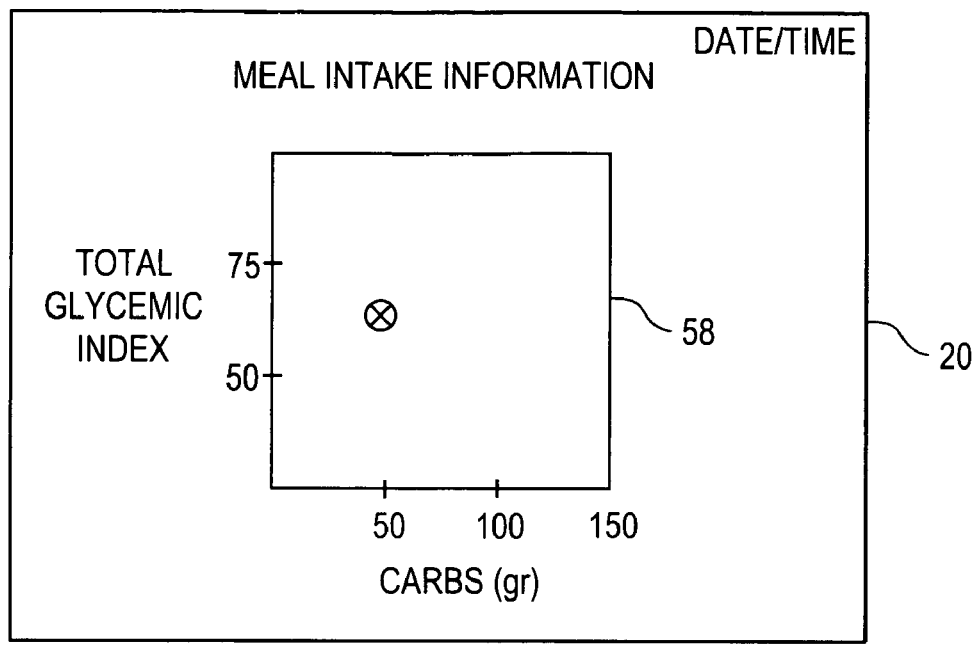
FIG. 6 illustrates still another embodiment of a graphical user interface for entering meal-related information into the system of FIG. 1.

Referring to FIG. 6, a further exemplary embodiment of a graphical user interface 58 providing for user input of meal intake information is shown. In the illustrated embodiment, the graphical user interface 58 defines a continuous function of the carbohydrate content, provided in the form of carbohydrate content by weight (in grams or other convenient weight units) and expected speed of overall glucose absorption from the meal by the patient provided in the form of a total glycemic index (dimensionless). Alternatively, the graphical user interface 58 could define a numeric display that is a discrete function of the carbohydrate content, provided in the form of carbohydrate content and expected speed of glucose absorption provided in the form of a total glycemic index. In either case, the carbohydrate content and/or total glycemic index parameters may alternatively be expressed in the graphical user interface 60 in the form of "large," "medium," and "small," as these terms are described hereinabove, or in the form of "larger than normal," "normal," and "smaller than normal," as these terms are described hereinabove. Any number of dotted, dashed, solid or other types of grid lines may alternatively or additionally be superimposed onto the graphical user interface 58 to facilitate discrimination between carbohydrate content and total glycemic index values on the interface 58. In any case, the graphical user interface 58 provides for a single user selection of carbohydrate content and expected speed of glucose absorption information relating to the meal that the patient is about to ingest, is ingesting, or has recently ingested. In the illustrated example, the user has selected a meal related input indicating that the meal that the patient is about to ingest, is ingesting, or has recently ingested has a carbohydrate weight of approximately 50 grams and a total glycemic index value of approximately 62.

Figure 7:
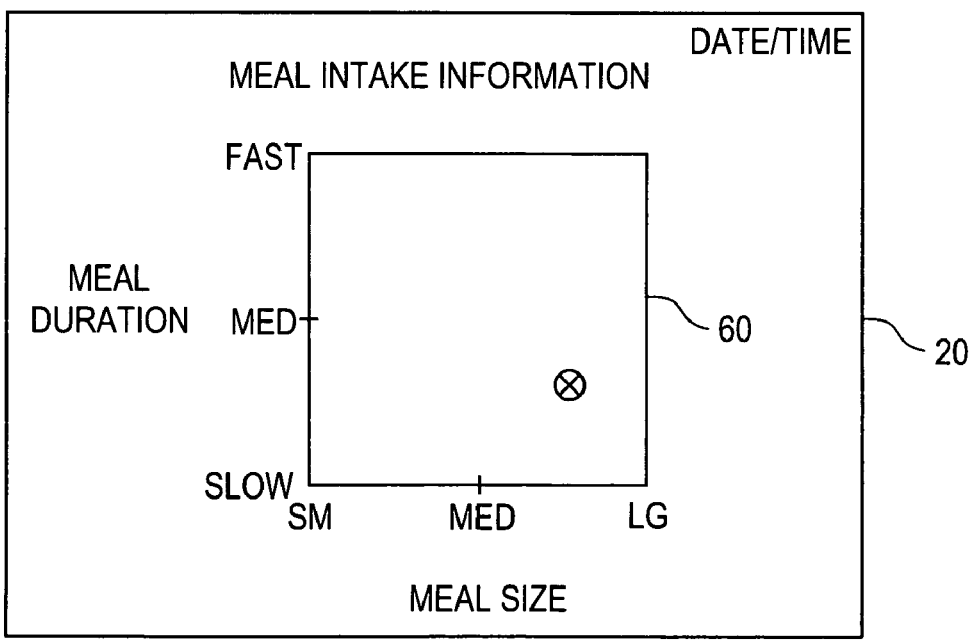
FIG. 7 illustrates yet a further embodiment of a graphical user interface for entering meal-related information into the system of FIG. 1.

Referring to FIG. 7, still another exemplary embodiment of a graphical user interface 60 providing for user input of meal intake information is shown. In the illustrated embodiment, the graphical user interface 60 defines a continuous function of the carbohydrate content, provided in the form of meal size, and expected speed of overall glucose absorption from the meal by the patient provided in the form of meal duration. The meal size axis defines three different meal size values in the form of "small", "medium" and "large" indicators, and the meal duration axis likewise defines three different meal duration values in the form of "slow", "medium" and "fast" indicators. The continuous-type graphical user interface 60 provides for a single user selection of carbohydrate content and expected speed of overall glucose absorption information relating to the meal that the patient is about to ingest, is ingesting, or has recently ingested. Any number of dotted, dashed, solid or other types of grid lines may alternatively or additionally be superimposed onto the graphical user interface 60 to facilitate discrimination between meal size and meal duration values on the interface 60. In the illustrated example, the user has selected a meal related input indicating that the meal that the patient is about to ingest, is ingesting, or has recently ingested is between medium and large size and ingested at a meal duration between slow and medium.

It will be noted that while the various examples of the graphical user interface depicted in FIGS. 2-7 were illustrated as being displayed on the display unit 20 of the electronic device 12, any of the graphical user interfaces may alternatively or additionally be displayed on the display unit 38 of the remote device 30. The display unit 20 in FIGS. 2-7 is further controlled by the processor 14 to display the current date and time in the upper right hand corner of the display unit 20. It will be understood that the processor 14 may be configured to alternatively control the display unit 20 in a conventional manner to display more or less information relating to the system 10; user and/or other desired information. It will further be understood that the various graphical user interfaces illustrated and described with respect to FIGS. 2-7 are provided only by way of example, and that various combinations of any one or more of the examples illustrated in FIGS. 2-7, as well as graphical user interfaces providing for the input of other carbohydrate content and glucose absorption shape, speed and/or duration information, may alternatively or additionally be used.

Figure 8:
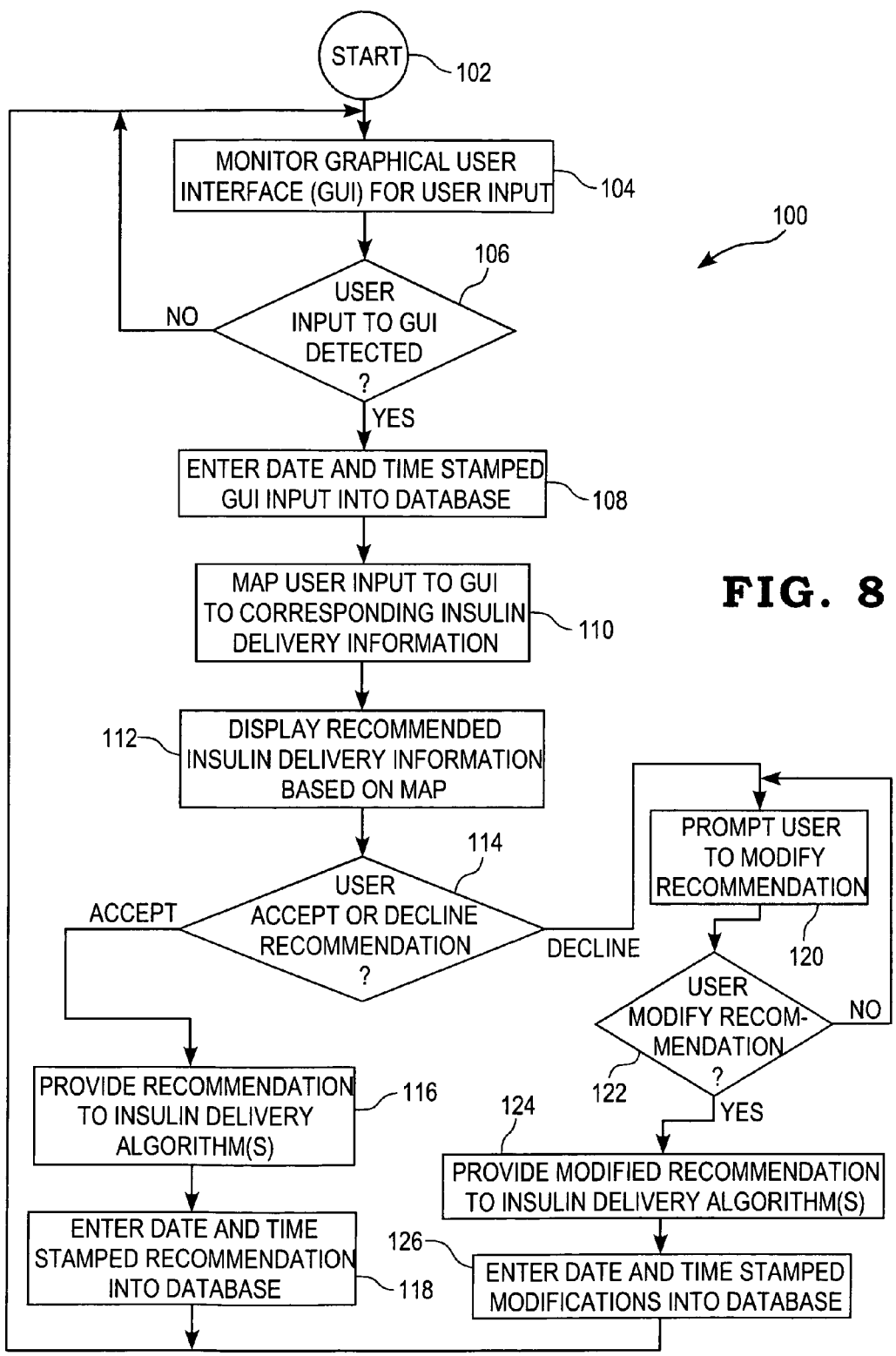
FIG. 8 is a flowchart illustrating one embodiment of a software algorithm, executable by the system of FIG. 1, for determining drug administration information based on user input of meal information using one of the graphical user interfaces of FIGS. 2-7.

Referring now to FIG. 8, a flowchart is shown of one illustrative embodiment of a software algorithm 100 for determining drug administration information, based on user input of meal intake information, using the system 10 of FIG. 1. The software algorithm 100 will be described as being executed by the processor 14 of the electronic device 12, although the software algorithm 100 may alternatively or additionally be executed by the processor 32 of the remote device 30. The algorithm 100 begins at step 102, and at step 104 the processor 14 is operable to monitor the graphical user interface (GUI) for user input of meal intake information. The graphical user interface may take the form of any one or any combination of the example graphical user interfaces illustrated and described herein with respect to FIGS. 2-7, or may alternatively take some other form providing for the user input of meal-related carbohydrate content and expected speed of overall glucose absorption from the meal by the patient.

Following step 104, the algorithm 100 advances to step 106 where the processor 14 is operable to determine whether a complete user input to the GUI has been detected. In embodiments having a single-input graphical user interface, for example, the processor 14 may be operable at step 106 to determine when a complete user input to the GUI has occurred when the user has selected a single input to the graphical user interface. In embodiments having a multiple-input graphical user interface, on the other hand, the processor 14 may be operable to determine when a complete user input to the GUI has occurred when the user has selected all user-selectable inputs to the GUI. In any case, if at step 106 the processor has not detected a complete user input to the GUI, execution of the algorithm 100 loops back to execute step 104. If, on the other hand, the processor 14 detects at step 106 that a complete user input to the GUI has occurred, algorithm execution advances to step 108 where the processor 14 is operable to time and date stamp the GUI input and to enter the date and time stamped GUI input into a database contained within the memory or data storage unit 16 and/or 34. Steps 104 and 106 may illustratively further include a timeout mechanism configured to direct the algorithm 100 to a specified step or state if the user does not provide a complete user input to the GUI within a specified time period.

In the illustrated embodiment, the algorithm 100 is arranged with the expectation that the user will enter the meal-related information just prior to ingesting the meal so that the date and time stamp is generally indicative of the date and time that the meal is actually consumed. Step 108 may illustratively be modified to further provide the user with the ability to modify the time and/or date associated with the date and time stamped GUI entry prior to entering this information into the database. This optional feature provides the user with the ability to enter the meal intake information into the GUI after ingesting the meal, and to then alter the time and/or date of the date stamp from the current time and/or date to reflect an actual or estimated previous time and/or date that the meal was ingested. In this manner, for example, meal compensation boluses may be determined and administered or recommended after the meal has been ingested. This optional feature also provides the user with the ability to enter the meal intake information into the GUI before ingesting the meal, e.g., sufficiently before the meal so that the date and/or time stamp of step 108 would generally not be indicative of the actual time and/or date that the corresponding meal is consumed, and to then alter the time and/or date stamp from the current time and/or date to reflect an estimated future time and/or date that the meal will likely be ingested. It should be understood, however, that in either case the algorithm 100 should further include one or more steps that allow the processor 14 to appropriately modify the user-entered input to the GUI for use in determining the meal compensation bolus so that the speed of overall glucose absorption from the meal by the patient takes into account the time elapsed between ingesting the meal and subsequently entering the meal-related user input to the GUI, or the time delay between entering the meal-related user input the GUI and subsequently ingesting the meal. Inclusion of such one or more steps would be a mechanical exercise for a skilled programmer.

Although not shown in FIG. 8, the algorithm 100 or another independently executing algorithm may further include one or more steps that allow the user to modify previously entered meal-related information and/or associated time and/or date stamp information, or to append new and/or perhaps more accurate information onto the previously entered meal-related information and/or associated time and/or date stamp information. This optional feature provides the user with the ability to modify such data, such as in cases where the meal-related information was entered prior to or during ingestion of the meal, to subsequently reflect any deviations in actual meal ingestion from that which was expected or estimated at the time the information was entered. For example, a scheduled meal may be skipped or delayed, more or less of the meal may have actually been consumed as compared with what was previously estimated, and/or the composition of the meal may have varied from what was previously estimated.

Figure 9:
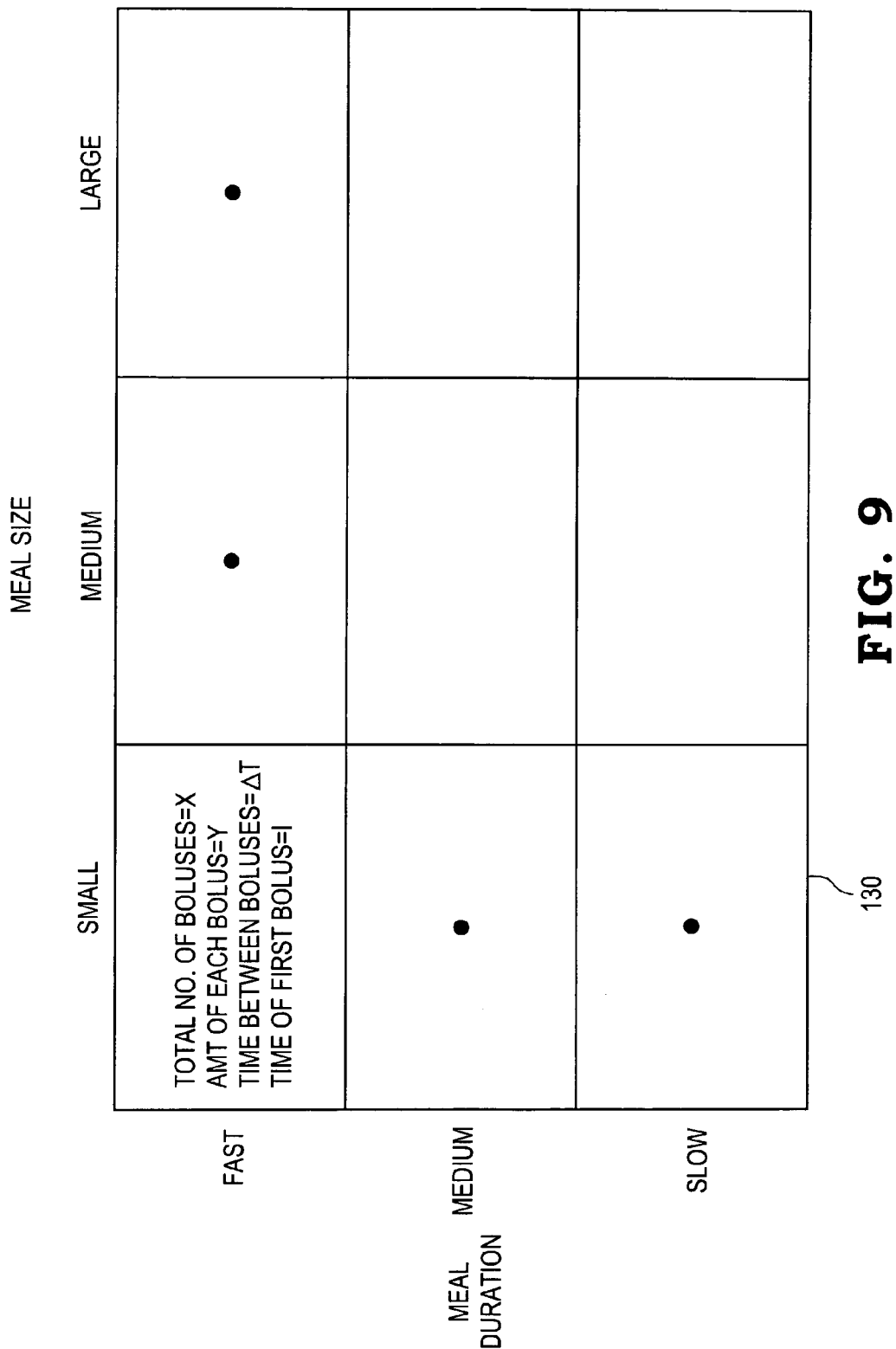
FIG. 9 is a table illustrating one embodiment of a map correlating user input of meal information, provided in the form of carbohydrate content, e.g., meal size, and expected glucose absorption shape and duration, e.g., meal duration, to corresponding drug administration information.

Following step 108, the processor 14 is operable at step 110 to map the user input of meal intake information to the GUI to corresponding insulin delivery information. The memory or data storage unit 16 and/or 34 illustratively has stored therein a map correlating the feed forward, user-entered meal information to insulin delivery amounts. The map may be provided in any conventional form, examples of which include, but are not limited to, one or more graphs, charts, tables, equations or the like. One exemplary embodiment of such a map 130 is shown in FIG. 9, and is provided in the form of a table mapping carbohydrate content, in the form of meal speed, and expected speed of overall glucose absorption from the meal by the patient, in the form of meal duration, to meal compensation bolus information. In the embodiment illustrated in FIG. 9, the meal compensation bolus information may be or include any one or more of a total number, X, of insulin boluses to be administered to the user, an amount or quantity, Y, of each of the number of insulin boluses to be administered (e.g., in international units), a time, $\Delta T$, between each of the insulin boluses to be administered and a time, I, that a first one of the number of insulin boluses will be administered. Those skilled in the art will recognize that other insulin dosing schemas may be used to define the map correlating the feed forward, user-entered meal information to insulin delivery amounts, and any such other insulin dosing schemas are contemplated by this disclosure.

Referring again to FIG. 8, the processor 14 is thus operable at step 110, in one illustrative embodiment, to map the user input to the GUI of meal intake information to insulin delivery information using a table of the general type illustrated in FIG. 9. It will be understood that the processor 14 may alternatively or additionally use different table axes values that are consistent with carbohydrate content and expected speed of overall glucose absorption from the meal by the patient, and/or use one or more other conventional mapping techniques for mapping the user-specified meal intake information to corresponding insulin bolus delivery information. While the insulin bolus delivery information was described with respect to FIG. 9 as comprising a meal compensation bolus including any one or more of total number, X, of insulin boluses to be administered to the user, an amount or quantity, Y, of each of the number of insulin boluses to be administered (e.g., in international units), a time, $\Delta T$, between each of the insulin boluses to be administered and a time, I, that a first one of the number of insulin boluses will be administered, it will further be understood that the insulin bolus delivery information may alternatively or additionally include one or more correction bolus amounts, i.e., insulin bolus amounts not related to meals, and in any case may include more or less information than that illustrated in FIG. 9.

Execution of the algorithm 100 advances from step 110 to step 112 where the processor 14 is operable, in the illustrated embodiment, to control the display unit 20 and/or display unit 38 to display, in the form of an insulin bolus recommendation, at least some of the insulin delivery information determined at step 110. Thereafter at step 114, the processor 14 is operable to determine whether the user accepts or declines the insulin bolus recommendation displayed at step 112. In one exemplary embodiment, the processor 14 is operable to execute step 114 by first displaying, along with the insulin bolus recommendation, graphical "accept" and "decline" indicators that are selectable by the user, and then monitoring such indictors to determine which of the two the user selects. In an alternative embodiment, "accept" and "decline" buttons or keys may form part of the input device 18 and/or 36, and the processor 14 is operable in this embodiment to execute step 114 by monitoring such buttons or keys to determine which of the two the user selects. Those skilled in the art will recognize other conventional techniques for accomplishing step 114, and any such other conventional techniques are contemplated by this disclosure. Step 114 may illustratively further include a timeout mechanism configured to direct the algorithm 100 to a specified step or state if the user does not accept or decline the recommendation displayed at step 112. In any case, if the processor 14 determines at step 114 that the user accepts the insulin bolus recommendation displayed at step 112, the processor 14 is thereafter operable at step 116 to provide the recommended insulin bolus information to one or more insulin delivery algorithms being executed by the processor 14, the processor 32 and/or one or more processor circuits forming part of any of the medical devices $26_1$-$26_N$. The processor 14, processor 32 and/or one or more processor circuits forming part of any of the medical devices $26_1$-$26_N$ is/are then operable to control, under the direction of any such one or more insulin delivery algorithms, automatic administration of one or more insulin boluses to the user according to the recommended insulin bolus information via a conventional electronically controlled insulin delivery device, e.g., implantable, subcutaneous, transcutaneous and/or transdermal insulin infusion pump. Alternatively, the user, health care professional or another individual may manually administer the one or more insulin boluses according to the recommended insulin bolus information via a conventional injection pen or other conventional manual delivery mechanism. Thereafter at step 118, the processor 14 is operable to date and time stamp the recommended insulin bolus information and enter the date and time stamped recommended insulin bolus information into a database contained within the memory or data storage unit 16 and/or 34.

If, at step 114, the processor 14 determines that the user rejects the insulin bolus recommendation displayed at step 112, the processor 14 is thereafter operable at step 120 to prompt the user to modify the recommended insulin bolus information. In one exemplary embodiment, the processor 14 is operable to execute step 120 by displaying the insulin bolus recommendation in a manner that allows the user to modify any of the recommended insulin bolus information via the graphical user interface, input device 18 and/or 36, or via some other conventional data input device, and to also display a graphical "accept changes" indicator that is selectable by the user when modifications to the recommended insulin bolus information are complete. The processor 14 is then operable at step 122 to monitor the "accept changes" indicator. Until the user selects the "accept changes" indicator at step 122, the algorithm 100 loops back to execute step 120. The algorithm may further illustratively include one or more conventional steps (not shown) that allow the algorithm 100 to continue past step 122 if the user does not select the "accept changes" indicator within a specified time period. In any case, when the processor 14 determines at step 122 that the user has selected the "accept changes" indicator, the processor 14 is thereafter operable at step 124 to provide the modified insulin bolus information to one or more insulin delivery algorithms being executed by the processor 14, the processor 32 and/or one or more processor circuits forming part of any of the medical devices $26_1$-$26_N$. The processor 14, processor 32 and/or one or more processor circuits forming part of any of the medical devices $26_1$-$26_N$ is/are then operable to control, under the direction of any such one or more insulin delivery algorithms, automatic administration of one or more insulin boluses to the user according to the modified insulin bolus information via a conventional electronically controlled insulin delivery device, e.g., implantable, subcutaneous, transcutaneous and/or transdermal insulin infusion pump. Alternatively, the user, health care professional or another individual may manually administer the one or more insulin boluses according to the modified insulin bolus information via a conventional injection pen or other conventional manual delivery mechanism. Thereafter at step 126, the processor 14 is operable to date and time stamp the modified insulin bolus information and enter the date and time stamped modified insulin bolus information into a database contained within the memory or data storage unit 16 and/or 34. In an alternate embodiment, steps 116-124 of the algorithm 100 may be modified in a conventional manner to allow the user to manually override the recommended insulin bolus information by manually administering one or more insulin boluses. In this embodiment, however, it is desirable to allow the user to enter into the database, at steps 118 and 126, date and time stamped information relating to the manual administration of the one or more insulin boluses, e.g., number, type, quantity and/or timing of the one or more insulin boluses. In any case, the execution of the algorithm 100 loops from either of steps 118 and 126 back to step 104.

In an alternative embodiment of the algorithm 100, steps 112-116 and 120-124 may be modified in a conventional manner to cause the processor 14 to control, under the direction of one or more insulin delivery algorithms, automatic administration of one or more insulin boluses to the user according to the insulin delivery information determined at step 110. In this embodiment, the insulin delivery information determined at step 110 is therefore not displayed or otherwise offered to the user as an insulin bolus recommendation, but is instead automatically administered or otherwise delivered to the user via a conventional electronically controlled insulin delivery device, e.g., implantable, subcutaneous, transcutaneous and/or transdermal insulin infusion pump.

The graphical user interface examples illustrated in FIGS. 2-7, as well as the algorithm 100 of FIG. 8 for determining drug administration information, based on user input of feed forward information via such a graphical user interface, have been presented herein in the context of supplying the system 10 with meal intake information from which insulin delivery information is determined. It will be understood that similar graphical user interfaces may alternatively or additionally be developed based wholly or in part on one or more other external influences and/or various physiological mechanisms associated with the user. Examples include, but are not limited to, considerations such as explicit or implicit one or two-dimensional indicators of exercise, stress, illness, menstrual cycle and/or the like. As one specific example, a graphical user interface of the type illustrated in FIGS. 2-7 may be developed to provide for user input of feed forward information in the form of user exercise information having one parameter or axis corresponding to relative (e.g., to a reference) or actual user exercise intensity and another parameter or axis corresponding to relative (e.g., to a reference) or actual user exercise duration, or having a single parameter or axis of user exercise information. As another example, a graphical user interface of the type illustrated in FIGS. 2-7 may be developed to provide for user input of feed forward information in the form of user stress information having one parameter or axis corresponding to relative (e.g., to a reference) or actual state or profile of user stress and another parameter or axis corresponding to relative (e.g., to a reference) or actual user stress duration, or having a single parameter or axis of user stress information. As yet another example, a graphical user interface of the type illustrated in FIGS. 2-7 may be developed to provide for user input of feed forward information in the form of user illness information having one parameter or axis corresponding to relative (e.g., to a reference) or actual state or profile of user illness and another parameter or axis corresponding to relative (e.g., to a reference) or actual user illness duration, or having a single parameter or axis of user illness information. As a further example, a graphical user interface of the type illustrated in FIGS. 2-7 may be developed to provide for user input of feed forward information in the form of user menstrual cycle information having one parameter or axis corresponding to relative (e.g., to a reference) or actual user menses severity and another parameter or axis corresponding to relative (e.g., to a reference) or actual menstrual duration, or having a single parameter or axis of user menstrual cycle information. Those skilled in the art will recognize examples of other graphical user interfaces that may be developed based on one or more other external influences and/or various physiological mechanisms associated with the user, and any such other examples are contemplated by this disclosure. In any case, the processor 14 is illustratively operable with any such graphical user interfaces to date and time stamp event occurrences, and may additionally allow the time and date stamp to be altered to identify that the one or more other external influences and/or various physiological mechanisms associated with the user occurred in the past or is expected to occur in the future. This feature also illustratively allows for the capability of providing the user with reminders of start/stop times of upcoming (e.g., scheduled) events in order to increase accuracy of the system and provide for an increased level of event compliance.

Graphical user interfaces of the foregoing type may be used, for example, by themselves to determine an amount, type and/or timing of delivery and/or recommendation of one or more drugs, e.g., insulin boluses. Alternatively, any such graphical user interfaces may be used, for example, along with one or more other graphical user interfaces, to modify an amount, type and/or timing of one or more insulin boluses. As a specific example of the latter case, the system 10 may be operable to determine and recommend and/or administer one or more insulin boluses based primarily on user input of meal intake information as described herein above using a graphical user interface of the type illustrated in FIGS. 2-7. One or more additional graphical user interfaces may also be provided to allow the user to adjust or modify the one or more insulin boluses using modification factors in the form of fractional multipliers, additive offset values and/or modification functions. As one specific example, an additional graphic user interface may be developed to provide for user input of feed forward information in the form of user exercise information having one parameter or axis corresponding to relative or actual user exercise intensity and another parameter or axis corresponding to relative or actual user exercise duration, having a single parameter or axis of user exercise information or having a single, user-selectable binary value that is representative of the occurrence or non-occurrence of user exercise in a particular time window relevant to the data being input. The memory or data storage unit 16 and/or 34, in this example, includes an additional map, such as of the type illustrated in FIG. 9, correlating user exercise intensity and duration to appropriate modification information. The processor 14 is then responsive to user input of the additional feed forward information in the form of user exercise information to modify the drug delivery information, previously determined by the processor 14 in accordance with the meal intake information, as a function of the modification information that is determined via the additional map. It will be understood that the additional map may be provided in any conventional form including for example, but not limited to, one or more graphs, plots, equations, tables or the like. As another example, an additional graphic user interface may be developed to provide for user input of feed forward information in the form of user stress information having one parameter or axis corresponding to relative or actual user stress state or profile and another parameter or axis corresponding to relative or actual user stress duration, having a single parameter or axis of user stress information or having a single, user-selectable binary value that is representative of the occurrence or non-occurrence of user stress in a particular time window relevant to the data being input. The memory or data storage unit 16 and/or 34, in this example, includes an additional map, such as of the type illustrated in FIG. 9, correlating user stress state or profile and duration to appropriate modification information. The processor 14 is then responsive to user input of the additional feed forward information in the form of user stress information to modify the drug delivery information, previously determined by the processor 14 in accordance with the meal intake information, as a function of the modification information determined via the additional map. It will be understood that the additional map may be provided in any conventional form including for example, but not limited to, one or more graphs, plots, equations, tables or the like. As yet another example, an additional graphic user interface may be developed to provide for user input of feed forward information in the form of user illness information having one parameter or axis corresponding to relative or actual user illness state or profile and another parameter or axis corresponding to relative or actual user illness duration, having a single parameter or axis of user illness information or having a single, user-selectable binary value that is representative of the occurrence or non-occurrence of user illness in a particular time window relevant to the data being input. The memory or data storage unit 16 and/or 34, in this example, includes an additional map, such as of the type illustrated in FIG. 9, correlating user illness state or profile and duration to appropriate modification information. The processor 14 is then responsive to user input of the additional feed forward information in the form of user illness information to modify the drug delivery information, previously determined by the processor 14 in accordance with the meal intake information, as a function of the modification information determined via the additional map. It will be understood that the additional map may be provided in any conventional form including for example, but not limited to, one or more graphs, plots, equations, tables or the like. As a further example, an additional graphic user interface may be developed to provide for user input of feed forward information in the form of user menstrual cycle information having one parameter or axis corresponding to relative or actual user menses severity and another parameter or axis corresponding to relative or actual menstrual duration, having a single parameter or axis of user menstrual cycle information or having a single, user-selectable binary value that is representative of the occurrence or non-occurrence of user menstrual cycle in a particular time window relevant to the data being input. The memory or data storage unit 16 and/or 34, in this example, includes an additional map, such as of the type illustrated in FIG. 9, correlating user menses severity and menstrual duration to appropriate modification information. The processor 14 is then responsive to user input of the additional feed forward information in the form of user menstrual cycle information to modify the drug delivery information, previously determined by the processor 14 in accordance with the meal intake information, as a function of the modification information determined via the additional map. It will be understood that the additional map may be provided in any conventional form including for example, but not limited to, one or more graphs, plots, equations, tables or the like. Those skilled in the art will recognize examples of other graphical user interfaces that may be developed based on one or more other external influences and/or various physiological mechanisms associated with the user, and any such other examples are contemplated by this disclosure.

Whether any one or more of the graphical user interfaces illustrated and described herein are suitable for use by a patient will depend, at least in part, upon that patient's personal habits. For example, whether a graphical user interface correlating meal intake information to meal-related insulin delivery information, as described hereinabove with respect to FIGS. 2-9, is suitable for use by a patient will depend, at least in part, upon the dietary habits of that patient. It is accordingly desirable to develop one or more appropriate graphical user interfaces for any patient based on that patient's habits and taking into account the patient's suitability for the use of any such graphical user interface based on such habits. In order to reduce the amount of input provided by the user to the system 10 without jeopardizing the overall level of glucose control, regularities in the user's eating habits are exploited. It can generally be expected that persons with diabetes typically choose from a relatively limited number of food items and combinations thereof. Whether or not a graphical user interface of the type illustrated and described herein is suitable for use by an individual depends generally on the ability to simplify the variability of meals or snacks in relation to their glycemic consequences by exploiting predictabilities in the individual's eating habits.

Figure 10:
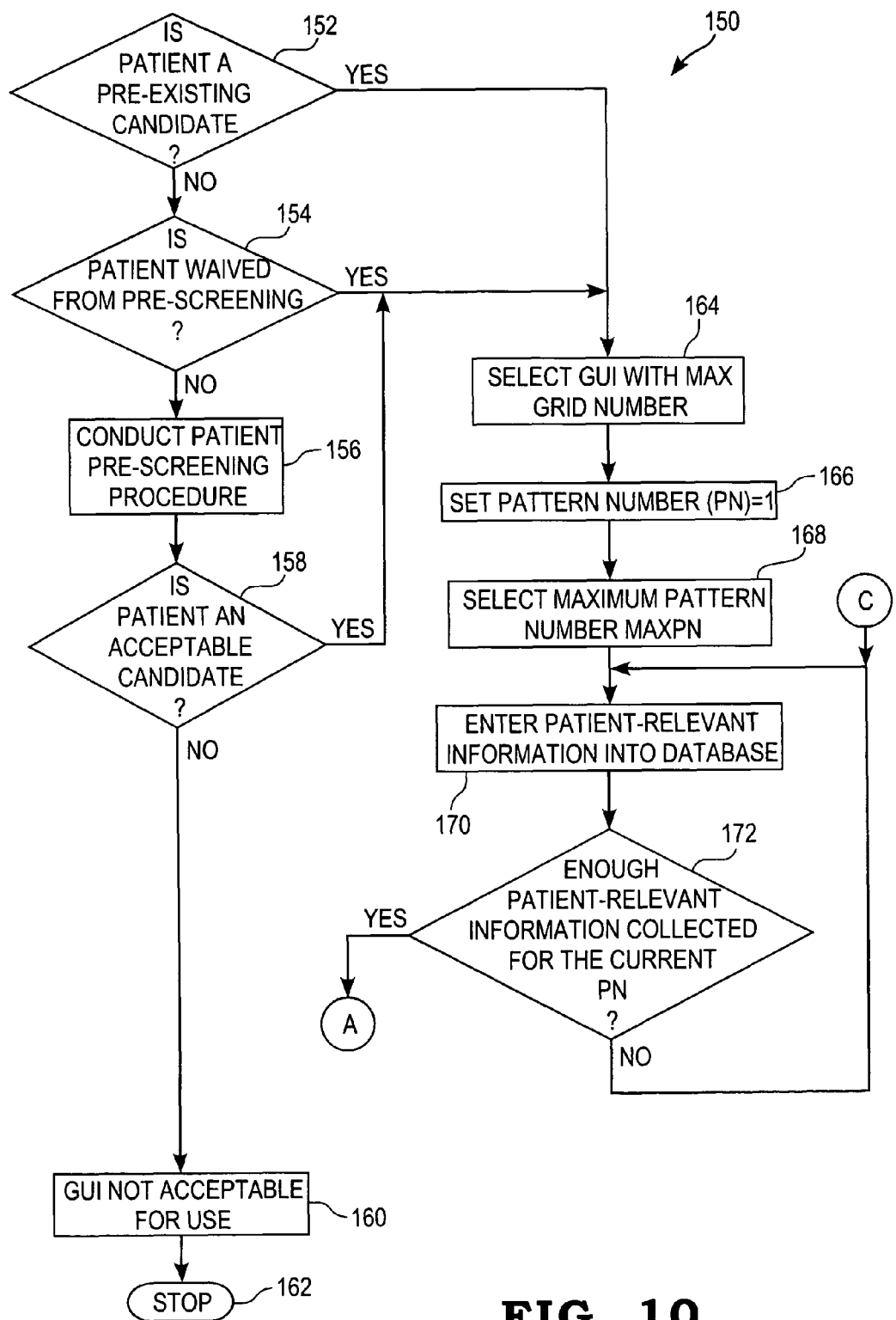
FIG. 10 is a flowchart of one illustrative process for determining patient or user suitability for use of a graphical user interface of the type illustrated in FIGS. 2-7.
Figure 11:
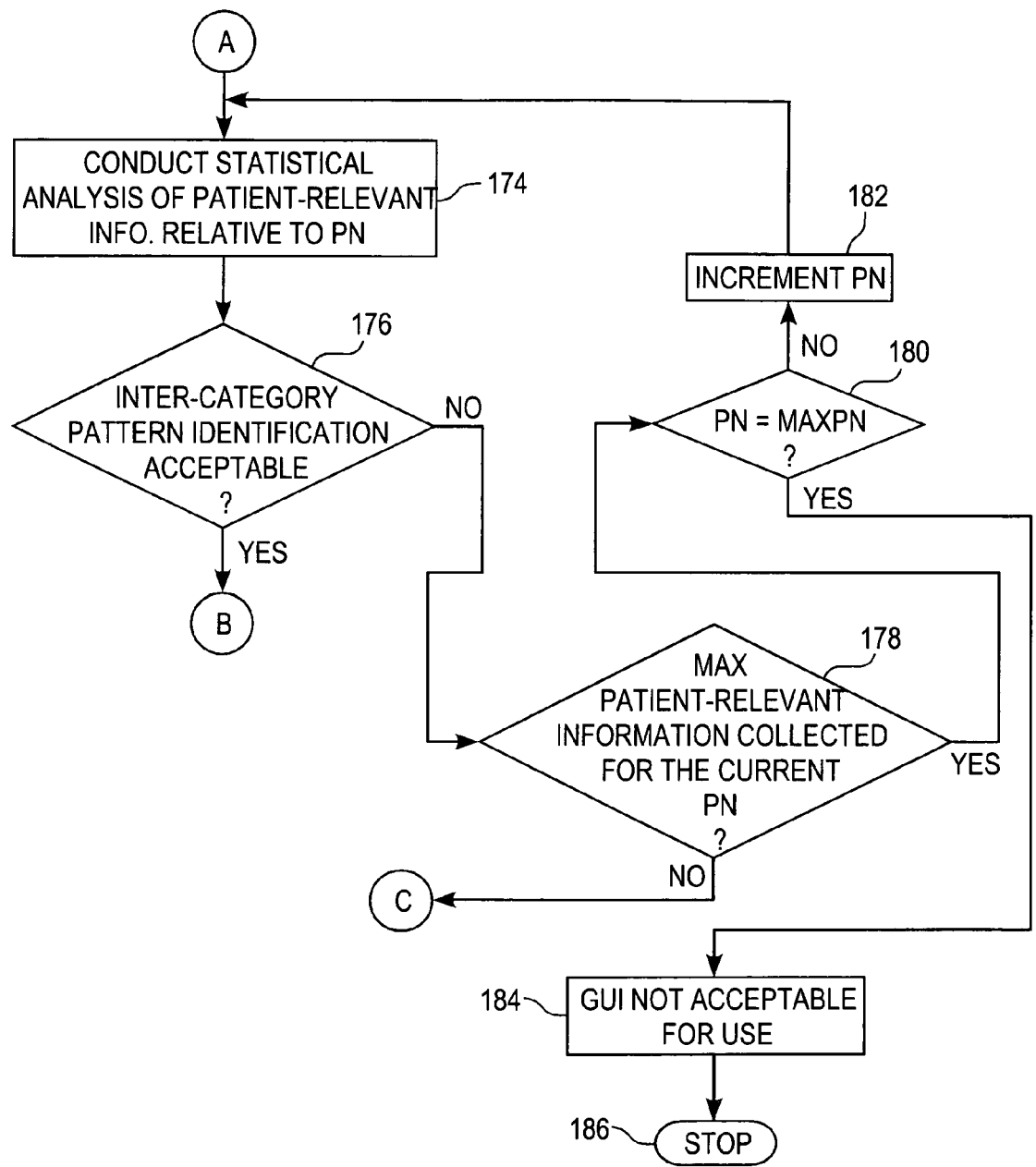
FIG. 11 is a continuation of the flowchart of FIG. 10.
Figure 12:
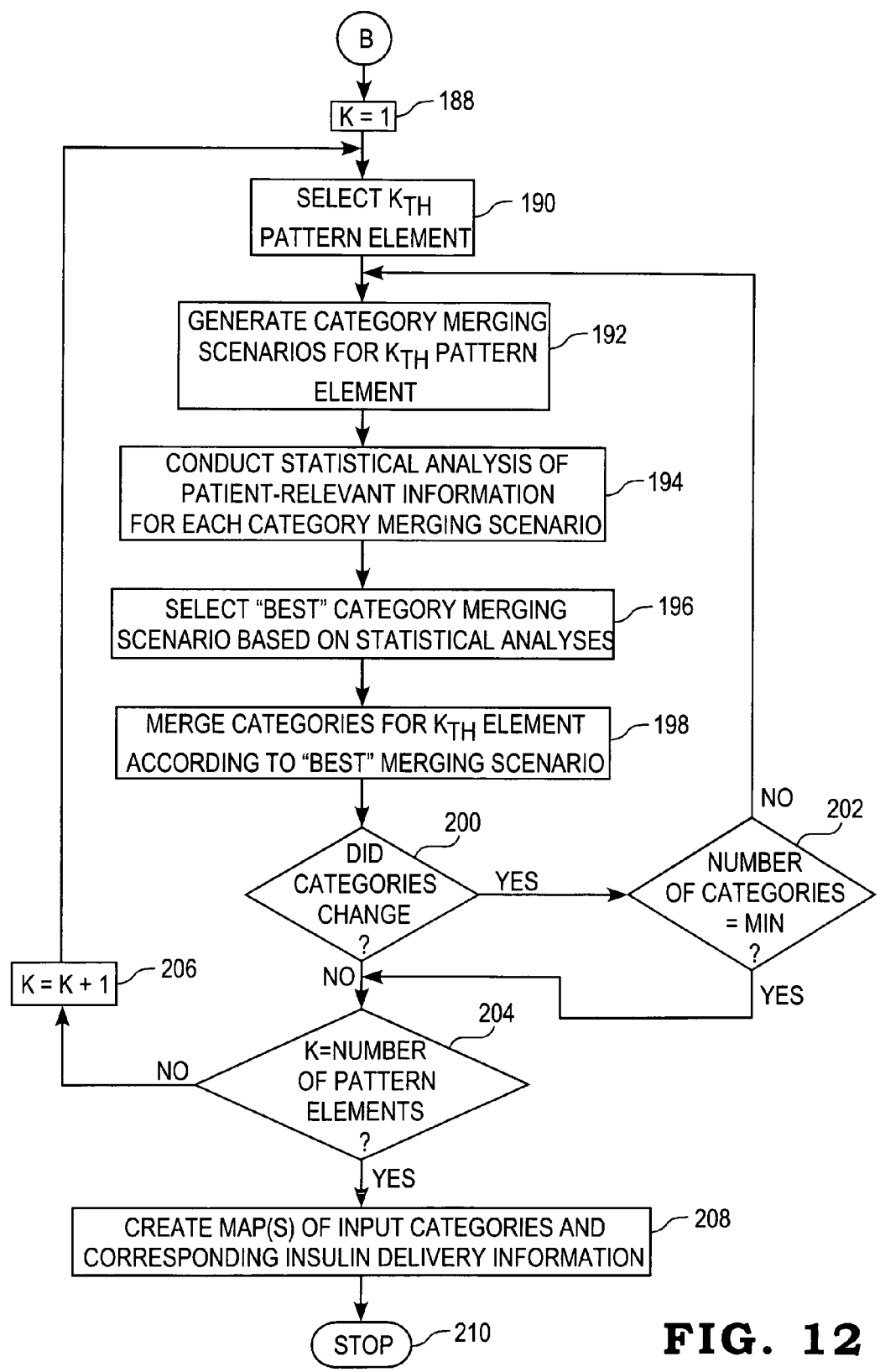
FIG. 12 is a continuation of the flowcharts of FIGS. 10 and 11.

Referring to FIGS. 10-12, a flowchart of one illustrative process 150 for determining patient or user suitability for using a graphical user interface of the type illustrated in FIGS. 2-7 is shown. In one exemplary embodiment, one or more of the steps of the process 150 are carried out manually. Alternatively or additionally, one or more of the remaining steps may be provided in the form of at least one software algorithm stored in a memory unit or data storage device, such as the memory unit or data storage unit 16 of the electronic device 12 or the memory unit or data storage device 34 of the remote device 30, and executed in a conventional manner by a processor, such as the processor 14 of the electronic device 12 or the processor 32 of the remote device 30. Alternatively still, the entire process 150 may be provided in the form of one or more software algorithms stored in a memory unit or data storage device, such as the memory unit or data storage unit 16 of the electronic device 12 or the memory unit or data storage device 34 of the remote device 30, and executed in a conventional manner by a processor, such as the processor 14 of the electronic device 12 or the processor 32 of the remote device 30.

In the illustrated embodiment, the process 150 is broken down into three process modules with each of the three modules illustrated separately in FIGS. 10, 11 and 12 respectively. The first process module is illustrated in flowchart form in FIG. 10, and relates to pre-screening patients for potential suitability for using a graphical user interface of the type illustrated in FIGS. 2-7, and to collecting patient-relevant information for the interface in cases where a determination of patient suitability for using the interface is made. The second process module is illustrated in flowchart form in FIG. 11, and relates to processing and analyzing the collected patient-relevant information to determine whether one or more regular patterns in the information can be identified that allow acceptable, i.e., sufficiently accurate, prediction of appropriate insulin delivery recommendations based on the available feed forward input categories. The third process module is illustrated in flowchart form in FIG. 12, and relates to analyzing the patient-relevant information, if one or more regular patterns in the information can be identified, with the goal of reducing, where appropriate, the number of feed forward input categories. In cases where the process 150 reveals that a suitable graphical user interface can be defined based on the patient's recorded dietary habits, the outcome of the third process module is a graphical user interface that maps user-selectable feed forward information to insulin delivery information.

Referring to FIG. 10, a flowchart of one illustrative embodiment of the first process module of the process 150 is illustrated. The process 150 starts at step 152 where it is determined whether the patient being considered for a graphical user interface of the type illustrated and described herein is a pre-existing candidate. Typically, step 152 will be conducted by a health care professional, and may be aided by a conventional computer with access to a patient records database. In any case, if it is determined at step 152 that the patient is a pre-existing candidate, algorithm execution advances to step 164. In such cases, the patient is a pre-existing candidate, and a health care professional has determined that the process 150 should be re-executed for the patient. If it is otherwise determined at step 152 that the patient is not a pre-existing candidate, algorithm execution advances to step 154.

At step 154, it is determined whether the patient being considered for a graphical user interface of the type illustrated and described herein, while not a pre-existing candidate, can be waived from a pre-screening process. Typically, step 152 will be conducted by a health care professional, and may be aided by a conventional computer. Generally, a patient may be waived from the pre-screening process if it appears to the health care professional that a graphical user interface of the type illustrated and described herein is suitable for use with the particular patient. While the health care professional may base such a determination on many factors, the health care profession will typically base the determination, at least in part, on an examination of the patient's meal habits, and may also take into account exercise habits, general health, patient stress, etc. As one example where a particular patient may be waived from the pre-screening process, the patient may follow a strict and repeatable diet as well as a regular exercise regimen. The health care professional, after examining the patient's diet and exercise regimen, may conclude that there is an acceptable likelihood that a graphical user interface of the type illustrated and described herein will be suitable for use with the particular patient, and that the pre-screening process may thus be waived. It will be understood that one or more other factors may alternatively or additionally be considered by the health care professional at step 154, and that the example just provided therefore should not be considered to be limiting in any way. In any case, if it is determined at step 154 that the patient may be waived from the pre-screening process, algorithm execution advances to step 164. If it is otherwise determined at step 154 that the patient may not be waived from the pre-screening process, algorithm execution advances to step 156.

At step 156, the health care professional conducts a patient pre-screening procedure to determine whether the patient may or may not be an acceptable candidate for a graphical user interface of the type illustrated and described herein. The pre-screening process, while it may include many factors for consideration, will typically include an examination of the various glucose affecting events that the patient manages (e.g., meals, stress, etc.) and how the patient manages these events (e.g., regular or irregular meal habits, exercise, insulin therapy, etc.). An example of one illustrative pre-screening procedure that may be conducted at step 156 is to have the patient and/or health care professional complete a worksheet or questionnaire designed to investigate patient information that is relevant to the determination of whether the patient may or may not be an acceptable candidate for a graphical user interface of the type illustrated and described herein. One exemplary questionnaire and/or worksheet may seek some or all of the following information:

1. The patient's daily and/or weekly meal schedule,
2. Meal amounts (e.g., by weight), 3. Composition of the various meals (e.g., amount of fat, protein and carbohydrates),
4. Glycemic index of the various meals,
5. Insulin dose schema for meal events,
6. Weekly habits (meal and non-meal related),
7. Exercise schedule,
8. Other lifestyle relevant information,
9. Patient's preference for using a graphical user interface of the type illustrated and described herein,
10. Issues with managing a quantity information on regular basis,
11. Patient's ability and desire to change meal and other habits so that variances in therapy needs are more acceptable for use with a graphical user interface of the type illustrated and described herein.

Information for each event, e.g. for each meal, is considered as a data record. A minimum number, m, of data records should be collected prior to conducting the pre-screening analysis, where "m" is the minimum number of data records in any particular pre-screening procedure that are needed in order to render useful results. Likewise, a limit on the maximum number of data records, n, may be imposed, where "n" may represent a practical maximum number of records, a number of records beyond which will not likely provide additional information, and/or a number of records beyond which will not likely contribute to the development of one or more patterns in the data where none currently exist.

The pre-screening procedure may also be used to collect event-specific therapy information which may include, but should not be limited to, one or more medications that the patient may currently be taking, one or more of various combinations of amount and intensity of therapy for given events, and timing of therapy. Information relating to the timing of therapy may include, but should not be limited to, one or more of the time of day and/or day of the week that the therapy is received or is undertaken, body rhythm information, e.g., menstrual cycle, etc., and combinational effects of factors such as exercise or stress on meals and insulin dose. Those skilled in the art will recognize other techniques for conducting a patient pre-screening procedure with the goal of determining whether the patient may or may not be an acceptable candidate for a graphical user interface of the type illustrated and described herein, and such other techniques are contemplated by this disclosure.

Following step 156, the health care professional evaluates at step 158 the patient relevant information collected during the patient pre-screening procedure, such as that set forth by example above, to determine whether the patient may or may not be an acceptable candidate for a graphical user interface of the type illustrated and described herein. In one embodiment, for example, the various entries of work sheet and/or questionnaire may be designed with point values so that a final "score" may be determined for the patient. In this example, whether or not the patient is an acceptable candidate for a graphical user interface of the type illustrated and described herein may be determined by comparing the patient's "score" on the questionnaire and/or worksheet with an established threshold score. In another embodiment, for example, the questionnaire and/or worksheet may be designed as a flowchart or tree structure that guides the health care professional through the questionnaire and/or worksheet and ultimately directs the health care professional to a conclusion that the patient is or is not an acceptable candidate for a graphical user interface of the type illustrated and described herein.

Those skilled in the art will recognize other techniques for evaluating a pre-screening questionnaire and/or worksheet, some of which may be conducted manually and others of which may be conducted with the assistance of a conventional computer, and any such other techniques are contemplated by this disclosure. In any case, if the health care professional determines at step 158 that the patient is an acceptable candidate for a graphical user interface of the type illustrated and described herein, the process 150 advances to step 164. If, on the other hand, the health care professional determines at step 158 that the patient is not an acceptable candidate for a graphical user interface of the type illustrated and described herein, the process 150 advances to step 160 where an indication is made that the graphical user interface is not acceptable for use with the patient being evaluated. In embodiments where steps 152-158 are conducted manually by a health care professional, step 160 may be omitted or merged with step 158. However, in embodiments where any one or more of the steps 152-158 are conducted with the assistance of a computer, step 160 may be implemented by displaying a suitable message, via such a computer, that the graphical user interface is not acceptable for use. Following step 160, the process 150 advances to step 162 where the process 150 ends.

From the "YES" branches of steps 152, 154 and 158, the process 150 advances to step 164 where a graphical user interface of the type illustrated and described herein is selected, and is selected to have a maximum grid size or number corresponding to a maximum number of user-selectable feed forward inputs on each axis of the graphical user interface. Generally, the maximum grid size number will depend upon several factors including, for example, but not limited to, ease of use, whether patients will be comfortable with using a graphical user interface having this number of feed forward inputs on each interface axis, how many feed forward inputs may be considered by patients to be too complicated, etc. In one embodiment, for example, the maximum grid number is five, although this number may be increased or decreased to suit the particular application. With a maximum grid number of five, this means that the carbohydrate content axis and the overall glucose absorption speed axis of the selected graphical user interface will each initially have five user-selectable inputs.

Following step 164, the process 150 advances to step 166 where a pattern number, PN, is set to one. Thereafter at step 168, a maximum pattern number, MAXPN, is selected. The pattern number, PN, as this term is used herein, relates to the number of different elements of the patient relevant information that are used to map the user-selectable feed forward inputs to corresponding insulin delivery information. For example, if the patient-relevant information is highly regular and repeatable, the graphical user interface may require only a single "meal" map that maps the user-selectable feed forward inputs to corresponding insulin delivery information for any meal taken at any time on any day of the week. As another example, if the patient-relevant information somewhat regular and repeatable, but is less regular and repeatable than in the last example, the graphical user interface may require a number of different "meal type" maps that each map the user-selectable feed forward inputs to corresponding insulin delivery information differently depending upon meal type, e.g., breakfast, lunch, dinner or snack. The maximum pattern number, MAXPN, imposes a limit on the number of different elements of the patient-relevant information that may be used to map the user-selectable feed forward inputs the corresponding insulin delivery information.

Following step 168, the process 150 advances to step 170 where information is collected about the patient relating to events defined by the feed forward inputs, and this information is entered into a database. In one exemplary embodiment, step 166 is carried out manually by having the patient keep a logbook, either in paper or electronic form, of events relevant to meal information and to a graphical user interface having the maximum grid number. One example of such a logbook 220, including example patient-relevant information, is illustrated in FIG. 13. In the illustrated example, the maximum grid number is five, so that the carbohydrate content axis and the overall glucose absorption speed axis will each have five selectable inputs. In the example logbook 220 of FIG. 13, the patient enters relevant information just prior to a meal or snack, and such relevant information may include, but should not be limited to, the patient's blood glucose just prior to the meal or snack, the meal type or category, e.g., "B" for breakfast, "L" for lunch, "D" for dinner and "S" for snack, estimated ingested (or to be ingested) carbohydrates, EIC, (e.g., in units of grams), an estimated meal effect duration, EMED, i.e., expected duration of the ingested food's effect on the individual's glucose level (e.g., in units of minutes), an absolute duration of the meal or snack, AMD, (e.g., fast, F, medium fast, MF, medium, M, medium slow, MS, or slow, S), a relative duration of the meal or snack, RMD, (e.g., longer than normal, LN, slightly longer than normal, SLN, normal, N, slightly slower than normal, SSN, or slower than normal, SN), an absolute size of the meal or snack, AMS, (e.g., large, L, medium large, ML, medium, M, medium small, MS, or small, S), a relative size of the meal or snack, RMS, (e.g., larger than normal, LN, slightly larger than normal, SLN, normal, N, slightly smaller than normal, SSN, or smaller than normal, SN), an absolute meal size in terms of fat content, AMSF (e.g., small, S, medium small, MS, medium, M, medium large, ML, or large, L), an absolute meal size in terms of carbohydrate content, AMSC, (e.g., small, S, medium small, MS, medium, M, medium large, ML, or large, L), an absolute meal size in terms of protein content, AMSP, (e.g., small, S, medium small, MS, medium, M, medium large, ML, or large, L), relative meal sizes in terms of fat, protein and carbohydrate content (not shown in FIG. 13) (e.g., smaller than normal, SN, slightly smaller than normal, SSN, normal, N, slightly larger than normal, SLN, or larger than normal, LN), total glycemic index of the meal or snack, TGI, any meal compensation bolus, MCB, administered prior to the meal or snack (e.g., I.U.), any correction bolus, CB, administered prior to the meal or snack (e.g., I.U.), date, time, and the like. Although not specifically shown in FIG. 13, other bolus-related information may be included in the log book when the meal compensation and/or correction boluses are administered in smaller doses over time. In such cases, the other bolus-related information may include, for example, but should not be limited to, number of meal compensation or correction boluses administered, amount of each bolus administered, time between administered boluses and time of administration of first bolus. Other information that may be relevant and that may accordingly be included in the patient logbook 220 includes, but is not limited to, exercise intensity and duration prior to the meal or snack, patient stress state (or profile) and duration prior to the meal or snack, patient illness intensity and duration prior to the meal or snack, menstrual cycle information, e.g., menses severity and menstrual duration prior to the meal or snack, and the like. Generally, it is desirable to collect such relevant patient information over an extended time period, e.g., at least four weeks for males and at least 6-8 weeks for females, although other time periods may alternatively be used.

It will be appreciated that no particular one of the graphical user interfaces illustrated and described hereinabove with respect to FIGS. 2-7 will be usable by all patients. Because habits, personal preferences and the like typically vary among patients, one or more of the graphical user interfaces may be well suited for some patients while others of the graphical user interfaces will be best suited for other patients. The particular information contained in the example log book illustrated in FIG. 13 will allow a physician or other diabetes care giver to subsequently choose any one of the graphic user interface examples illustrated and described hereinabove with respect to FIGS. 2-7. In cases where fewer graphical user interfaces are available, the information contained in the example log book illustrated in FIG. 13 may likewise be reduced.

In another exemplary embodiment wherein the events are meals ingested by the patient, step 170 of the process 150 is carried out by having a dietician or other meal planner provide the information illustrated by example in FIG. 13 based on specifically planned meal types, contents and times. In any case, execution of the process 150 advances from step 170 to step 172 where a determination is made as to whether enough patient-relevant information has been collected for the current pattern number. If so, the process 150 advances to the second process module "A." If, at step 172, it is determined that an insufficient amount of patient-relevant information has been collected for the current pattern number, the process 150 loops back to step 170.

As described hereinabove with respect to the pre-screening procedure of step 156, a minimum number, m, of data records should be collected prior to advancing to second process module, where "m" is the minimum number of data records that are needed in order to render useful results. Likewise, a limit on the maximum number of data records, n, is imposed by step 172, where "n" may represent a practical maximum number of records, a number of records beyond which will not likely provide additional information, and/or a number of records beyond which will not likely contribute to the development of one or more patterns in the data where none currently exist.

Referring now to FIG. 11, a flowchart of one illustrative embodiment of the second process module of the process 150 is illustrated. The second process module begins at step 174 where a series of statistical analyses are conducted on the patient relevant information collected at step 168 with the goal of finding a starting pattern number that has a significant impact on the user's meal category (i.e., user-selected feed forward information). Thereafter at step 176, a determination is made as to whether the inter-category pattern identification resulting from the statistical analysis is acceptable. If so, the process 150 advances to the third process module "B." If, however, the inter-category pattern identification resulting from the statistical analysis of step 174 is not acceptable, the process 150 advances to step 178 where a determination is made as to whether enough patient-relevant information has been collected for the current pattern number. If not, the process 150 returns to step 170 of FIG. 10. If, on the other hand, a determination is made at step 178 that enough patient-relevant information has been collected for the current pattern number, the process 150 advances to step 180 where a determination is made as to whether the pattern number, PN, is equal to the maximum pattern number, MAXPN. If not, the pattern number, PN, is incremented at step 182 and the process 150 then loops back to step 174. If, however, the pattern number, PN, is equal to the maximum pattern number, MAXPN, at step 180, the process 150 advances to step 184 where an indication is made that the graphical user interface is not acceptable for use with the patient being evaluated. In embodiments where the steps 174-182 are conducted manually by a health care professional, step 184 may be omitted or merged with step 182. However, in embodiments where any one or more of the steps 174-182 are conducted with the assistance of a computer, step 184 may be implemented by displaying a suitable message, via such a computer, that the graphical user interface is not acceptable for use. Following step 184, the process 150 advances to step 186 where the process 150 ends.

One illustrative example of the loop in the second process module comprising steps 174-180 involves the iterative modeling of the given meal compensation bolus as a function of the independent variables (meal type, day of the week, selected input grid classification, etc. The maximum absolute or relative prediction error could then be used as measure of the suitability when compared to a predefined limit.

Another illustrative example of the loop in the second process module comprising steps 174-182 is illustrated in FIGS. 14A-14K. The example illustrated in FIGS. 14A-14K makes use of a metric in the form of a coefficient of variation (CV) as measure for the inter-category pattern identification in the form of a spread of the bolus response, and applies an iteratively finer pooling of the patient-relevant information until the maximum CV does not exceed a predefined acceptable value. If this condition cannot be reached the grid-type user interface may not be suitable for the user.

To illustrate the approach of FIGS. 14A-14K, consider a reduction of a grid-type graphical user interface, of the type illustrated and described herein, to one dimension defining the carbohydrate content of a meal in the form of three categories (classifications), e.g. "less than normal", "normal", and "more than normal." A maximum value CVmax (e.g. CVmax=10%) is then chosen.

The statistical analyses of the user relevant information, such as that illustrated by way of example in FIG. 13, are illustratively performed in four steps. At step 1 the collected data are sorted by the size category ("less than normal", "normal", "more than normal") which corresponds to pooling the data across all other variables as illustrated in FIG. 14A. For each of these categories the coefficient of variation, CV, is calculated using known techniques. If none of the calculated coefficients, CV, exceed CVmax, the user interface is suitable for the user. In such a case the feed forward input to the graphical user interface would be, in the one-dimensional case, a meal size value only, e.g., less, more or normal, for a pending meal. The feed forward information-to-insulin bolus information map of FIG. 9 may then, for example, be a single map that maps the user-selected feed forward input values of meal size to corresponding insulin bolus information for any meal taken at any time and on any day of the week. The corresponding insulin bolus information, in this case, may be, for example, an insulin bolus profile equal to the average bolus profile for the user-specified category of meal size using the information from the statistical analysis step 1 of FIG. 14A.

Figure 14B:
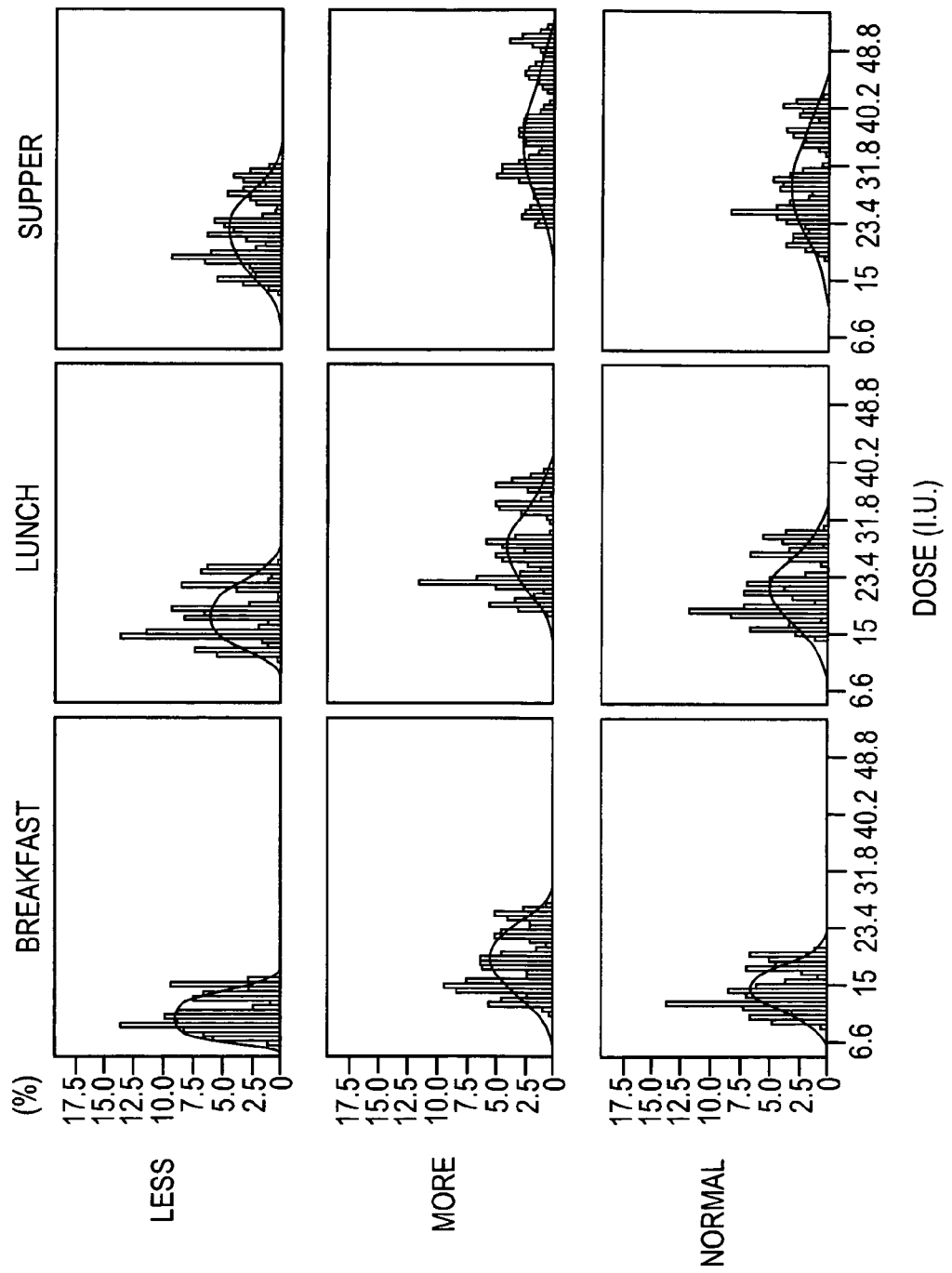

In this example, one or more of the calculated coefficients, CV, from step 1 (FIG. 14A) exceed CVmax, and the statistical analyses process accordingly advances to step 2. At step 2, the collected data are sorted by the size categories ("less than normal", "normal", "more than normal") and by the meal type or time (breakfast, lunch, and dinner), as illustrated in FIG. 14B, which corresponds to pooling the data across all other variables. The coefficient of variation, CV, is then calculated by meal size category and meal type or time. If none of the calculated coefficients exceeds CVmax the user interface is suitable for the user. In such a case the forward inputs to the graphical user interface would be, in the one dimensional case, a meal size value and a meal type or time value for a pending meal. The feed forward information-to-insulin bolus information map of FIG. 9 may then, for example, include three maps that each maps the user-selected feed forward input values of meal size to different corresponding insulin bolus information depending upon meal type or time, e.g., breakfast, lunch or dinner. The corresponding insulin bolus information, in this case, may be, for example, an insulin bolus profile equal to the average bolus profile, by meal type or time, for the user-specified categories of meal size using the information from the statistical analysis step 2 of FIG. 14B.

Figure 14C:
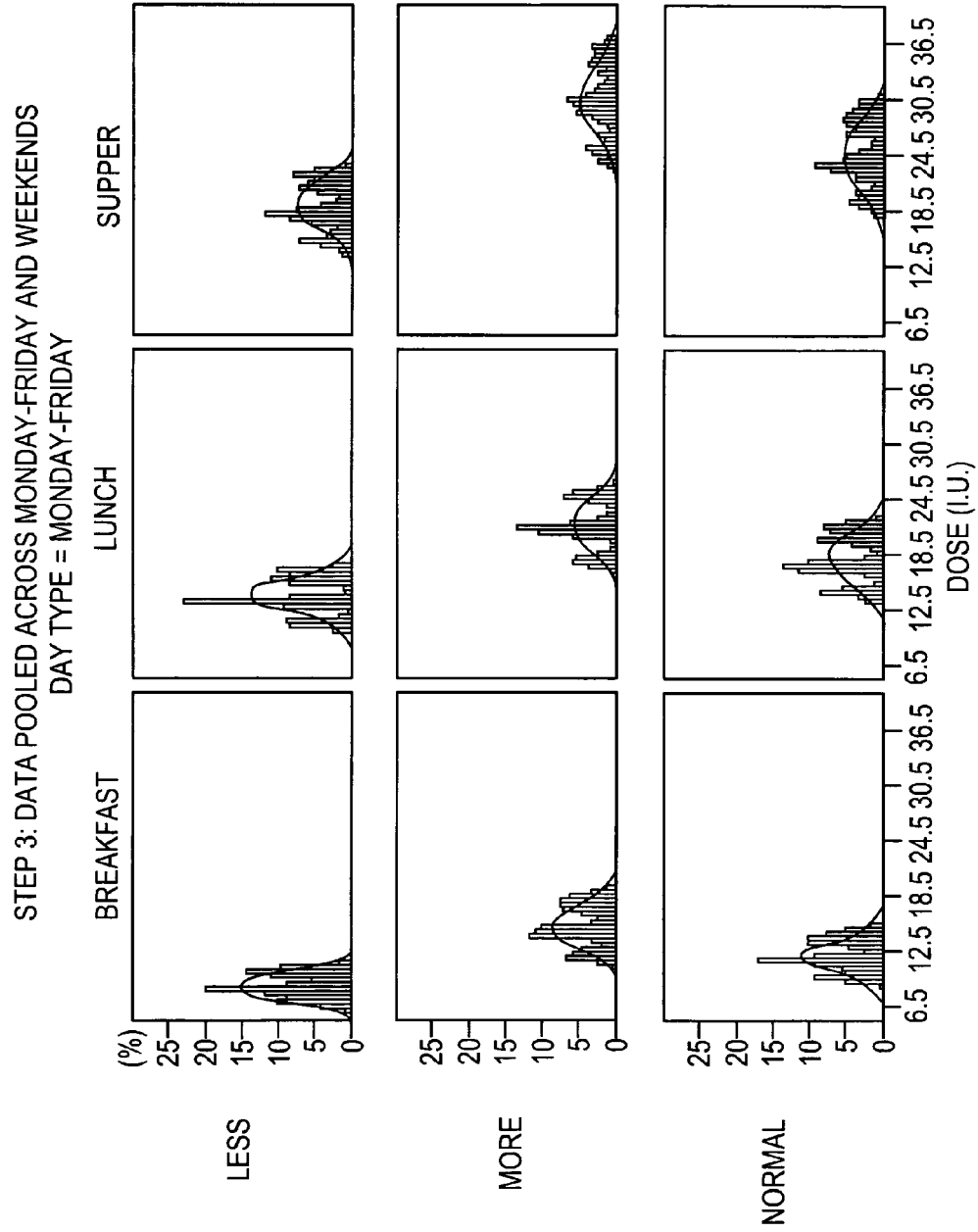
Figure 14D:
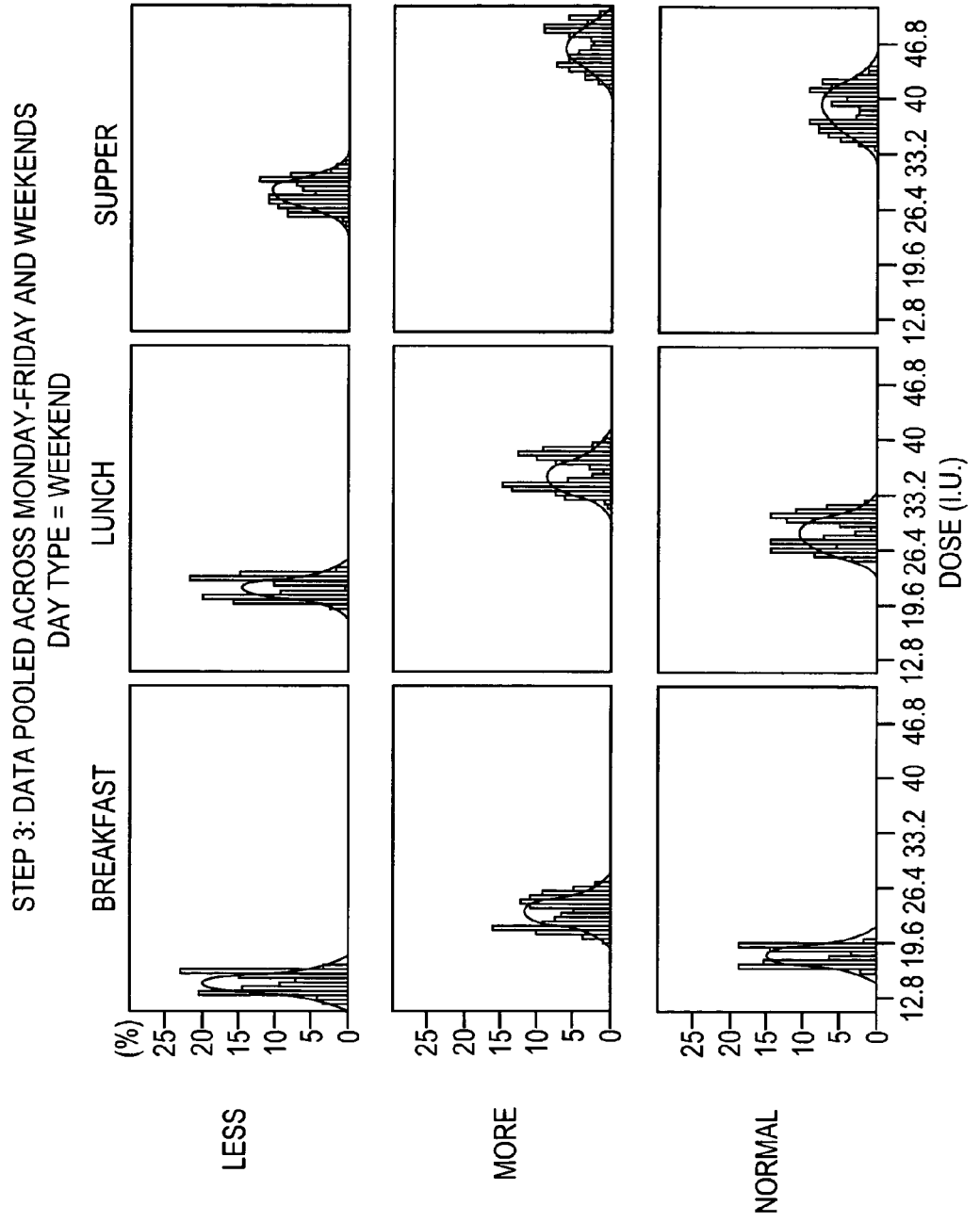
Figure 14E:
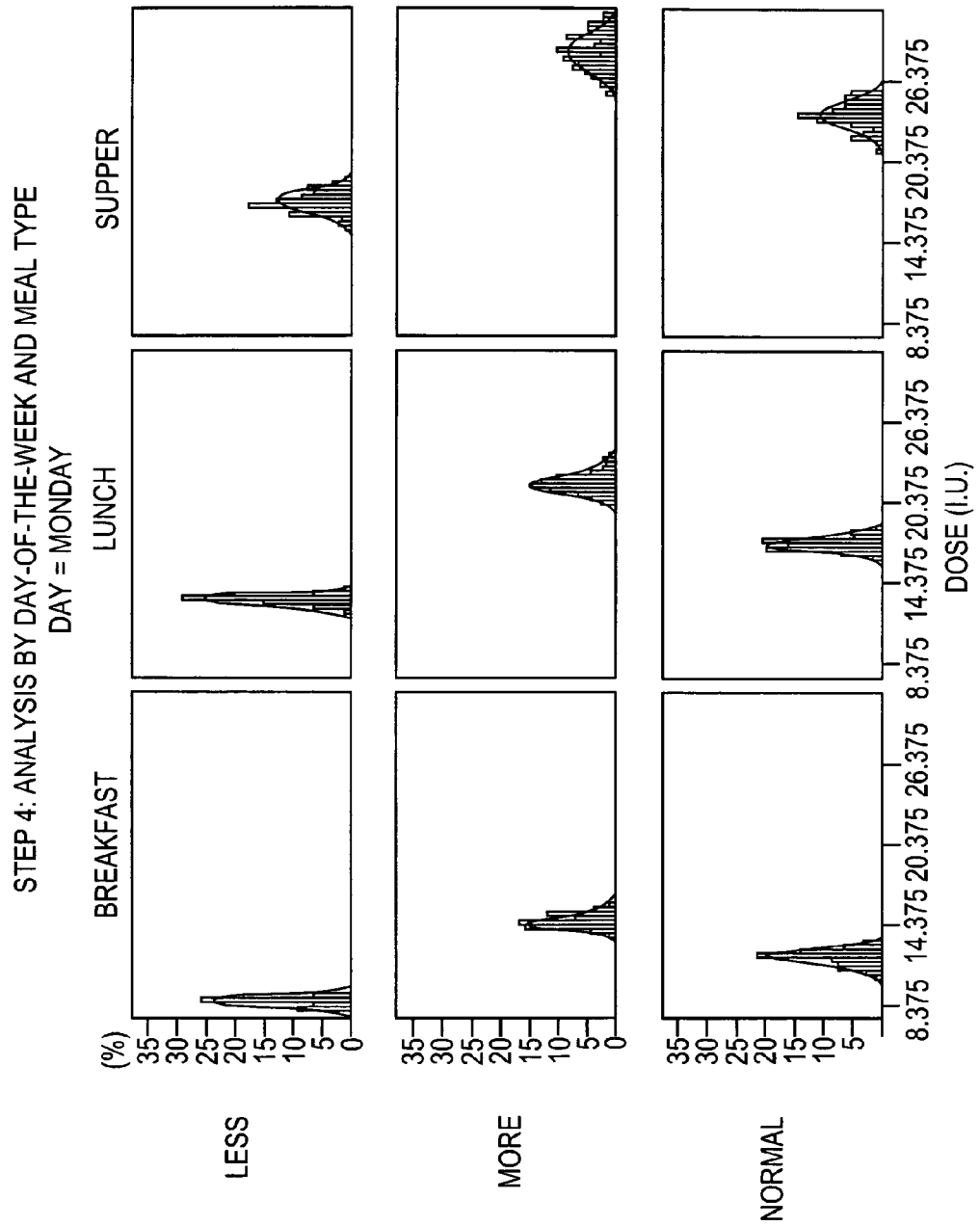
Figure 14F:
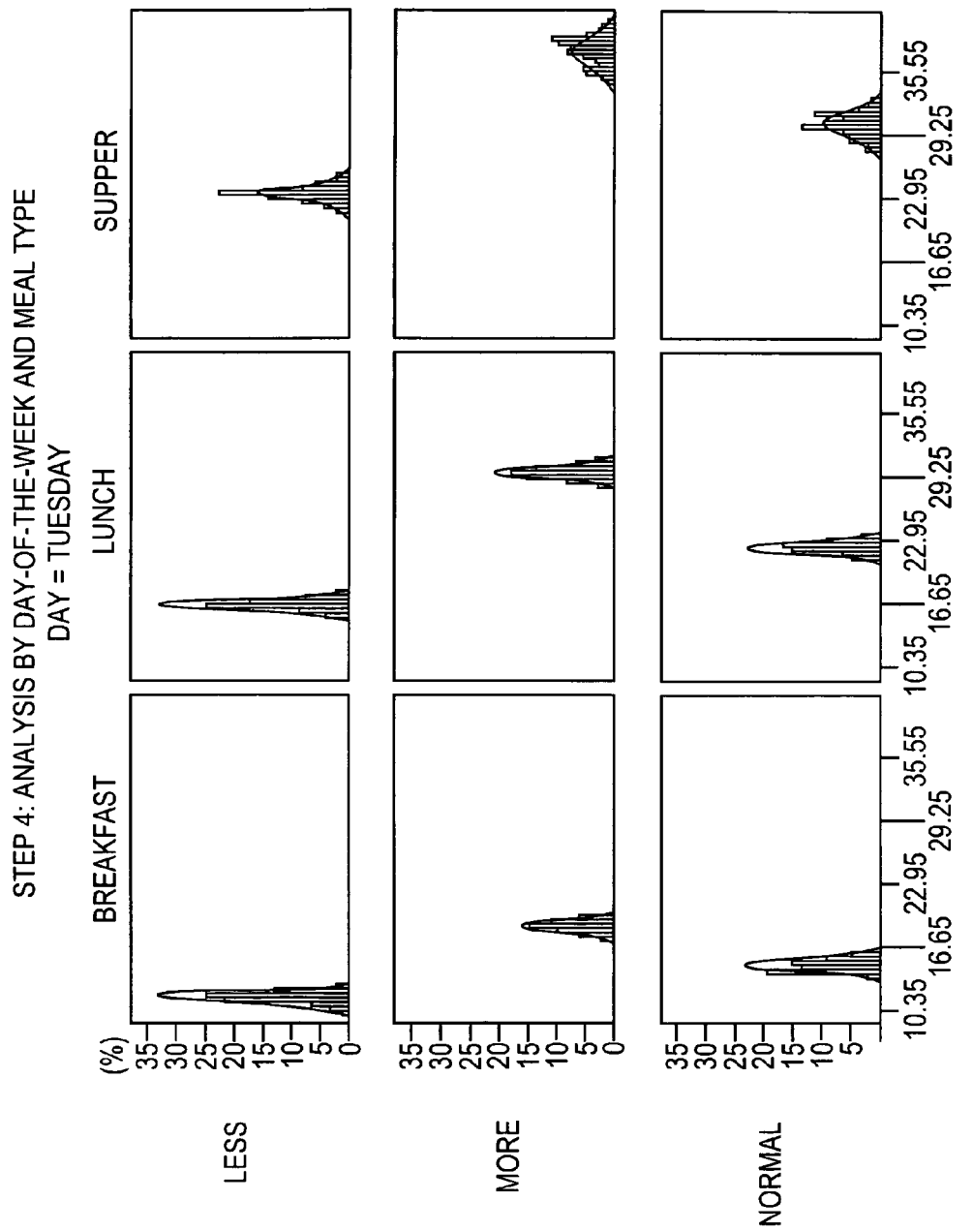
Figure 14G:
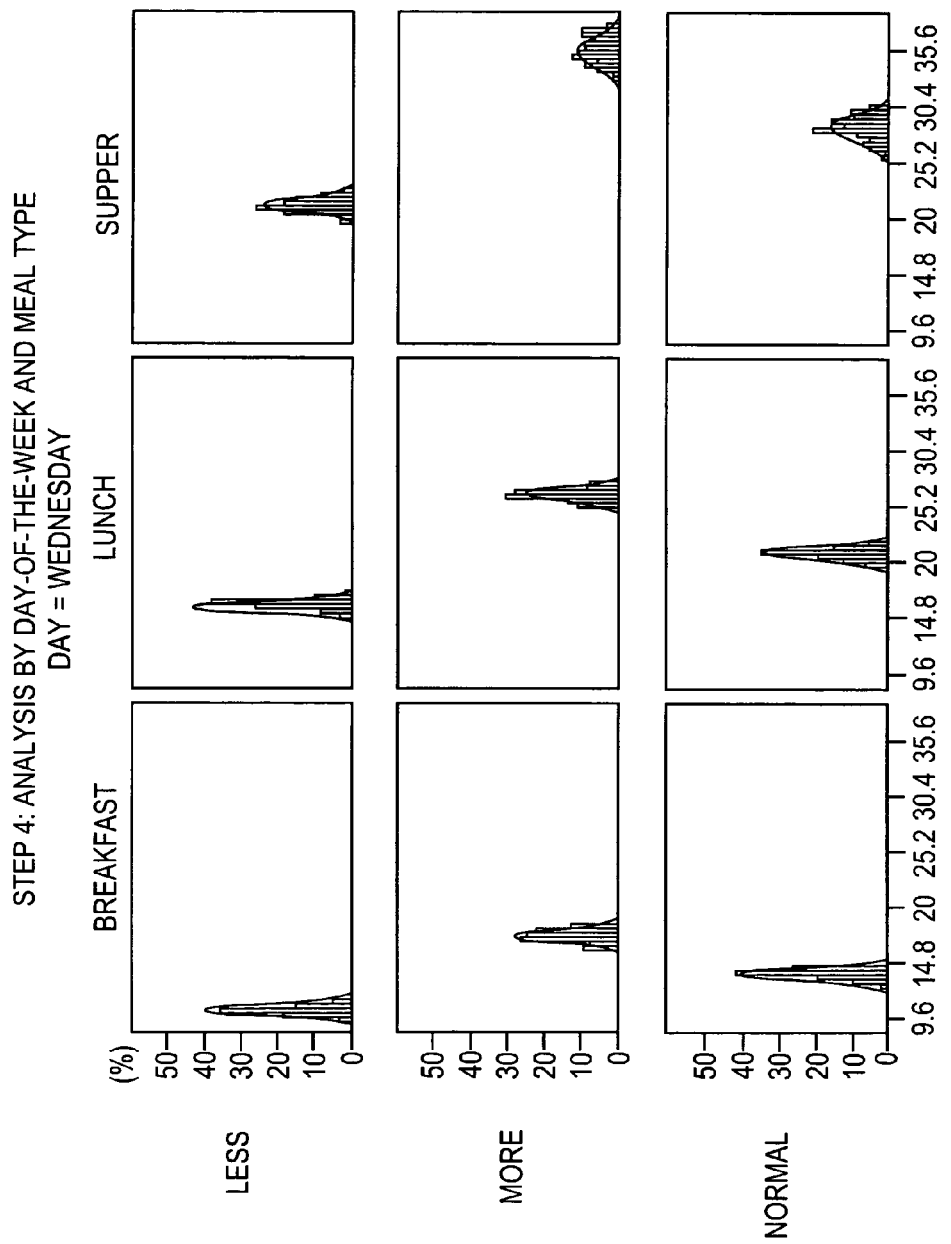
Figure 14H:
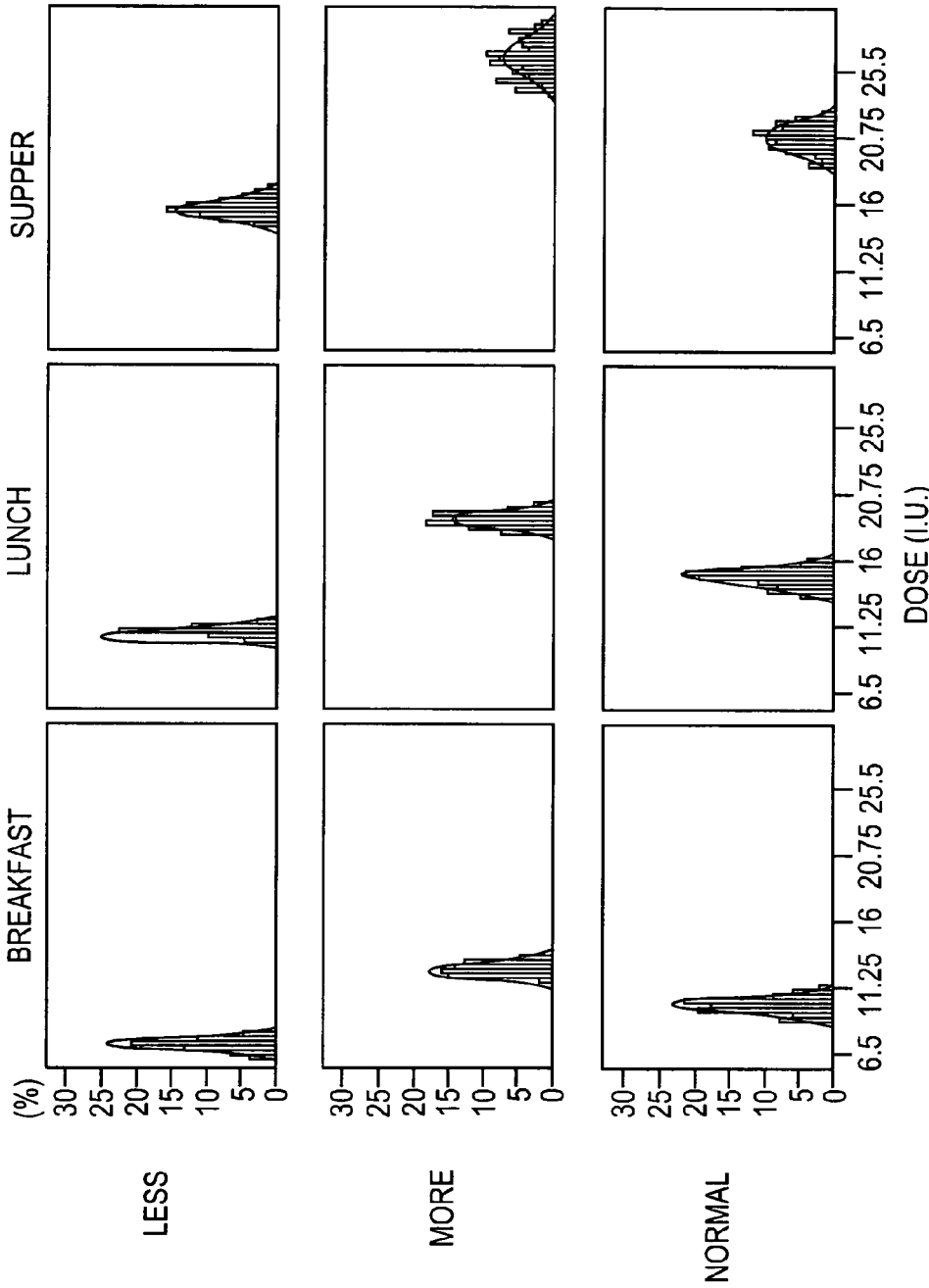
Figure 14I:
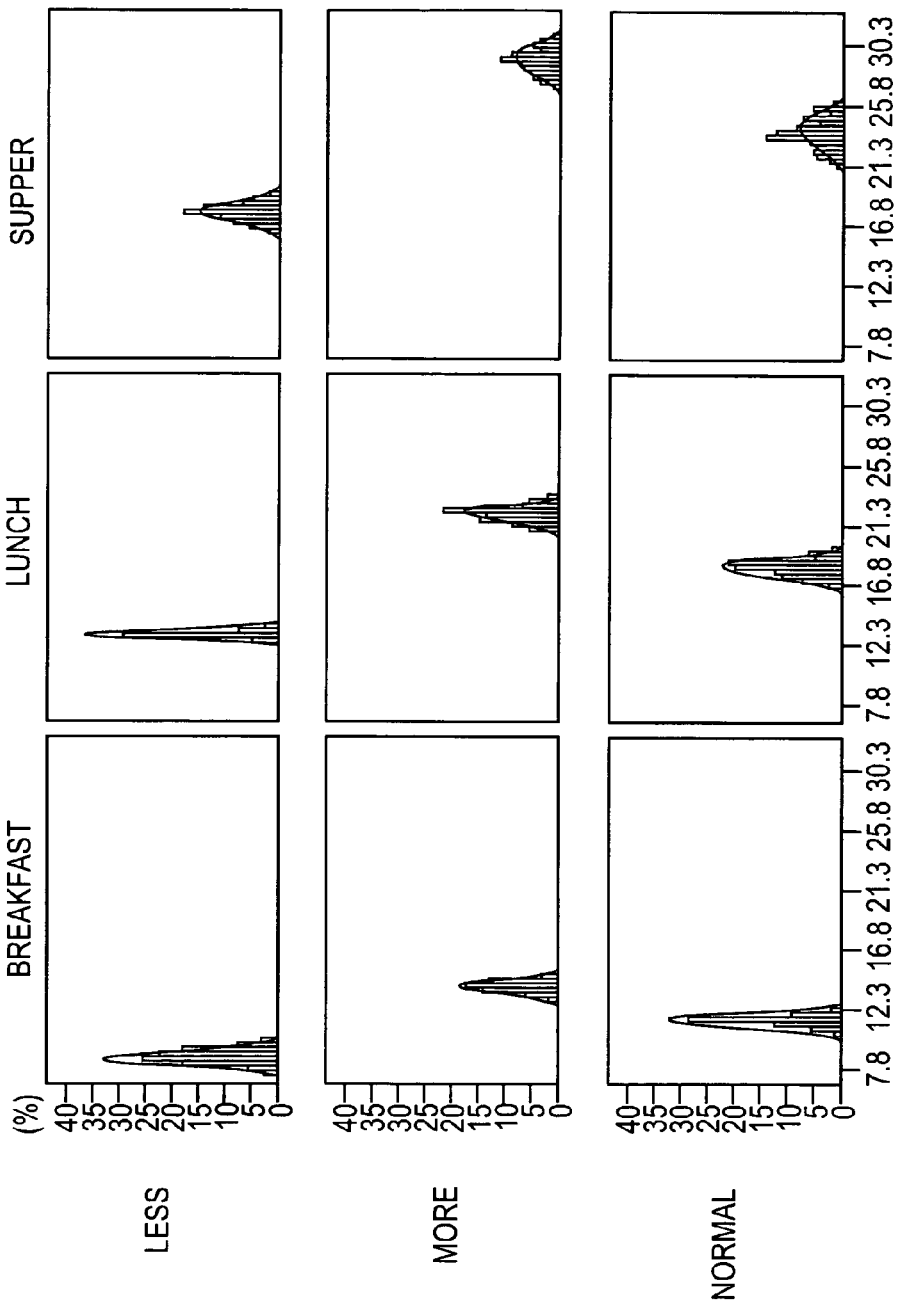
Figure 14J:
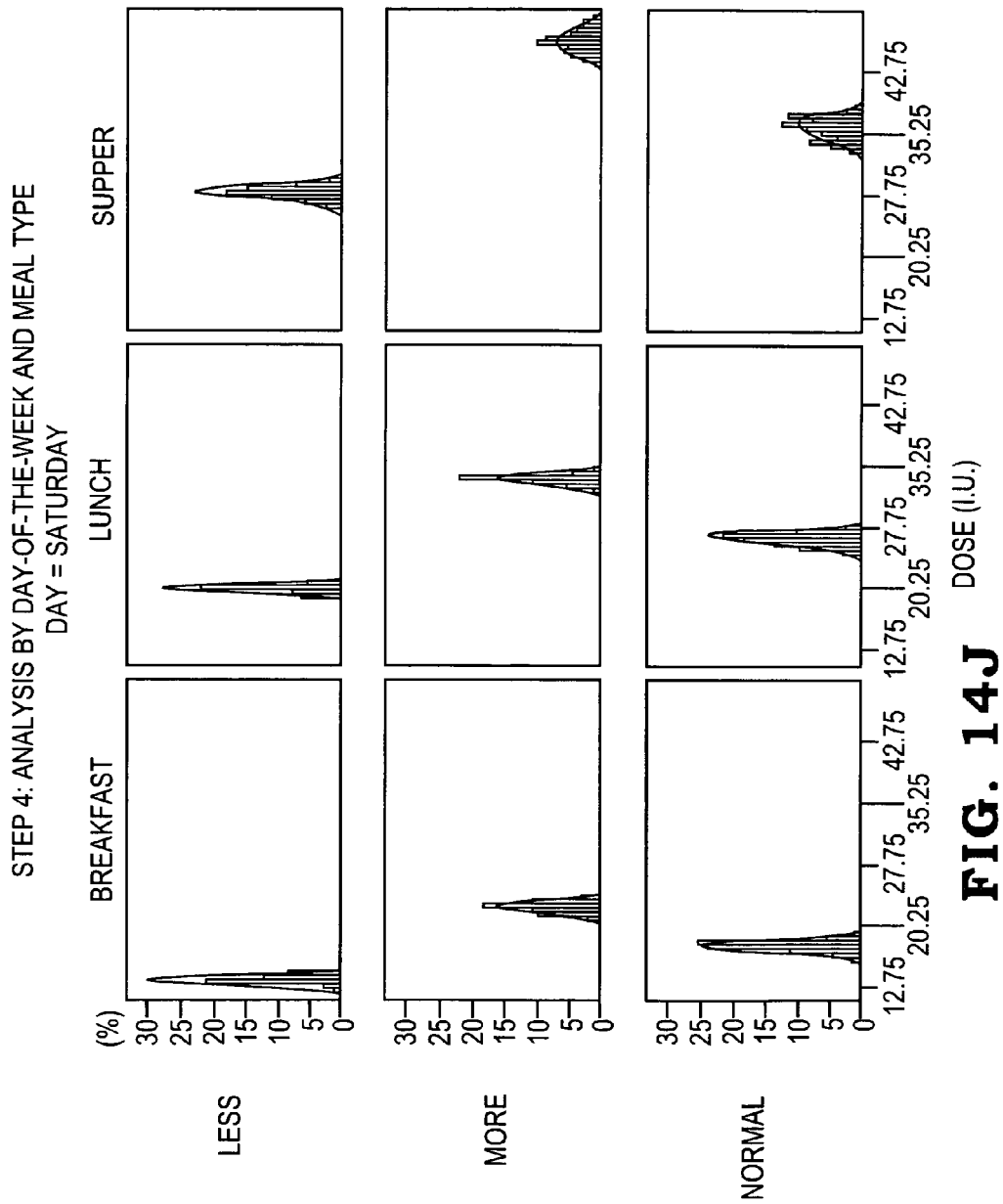
Figure 14K:
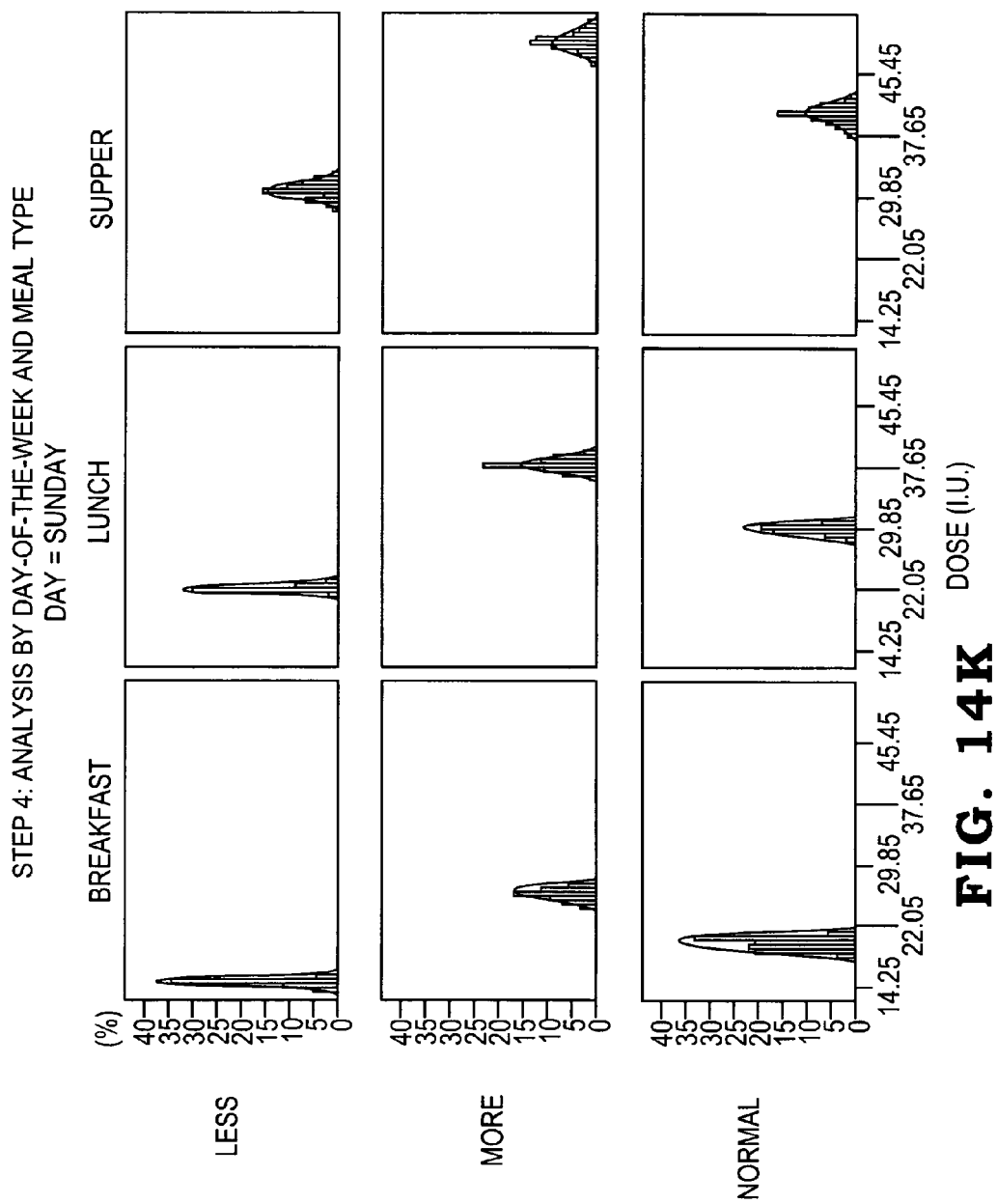

In this example, one or more of the calculated coefficients, CV, from step 2 (FIG. 14B) exceed CVmax, and the statistical analyses process accordingly advances to step 3. At step 3 the collected data are sorted by the size categories ("less than normal", "normal", "more than normal"), the meal type or time (breakfast, lunch, and dinner), and the type of day (weekday, weekend), as illustrated in FIGS. 14C and 14D, which corresponds to pooling the data across all other variables. The coefficient of variation is calculated by size category, meal type or time, and type of day. If none of the calculated coefficients exceeds CVmax the user interface is suitable for the user. In such a case the feed forward inputs to the graphical user interface would be, in the one dimensional case, a meal size value, a meal type or time value and a day type value for a pending meal. The feed forward information-to-insulin bolus information map of FIG. 9 may then, for example, include six maps that each map the user-selected feed forward input values of meal size to different corresponding insulin bolus information depending upon meal type or time, e.g., breakfast, lunch or dinner and also depending upon day type, e.g., week day or weekend. The corresponding insulin bolus information, in this case, may be, for example, an insulin bolus profile equal to the average bolus profile, by meal type or time and also by day type, for the user-specified categories of meal size using the information from the statistical analysis step 3 of FIGS. 14C and 14D.

In this example, one or more of the calculated coefficients, CV, from step 3 (FIGS. 14C and 14D) exceed CVmax, and the statistical analyses process accordingly advances to step 4. At step 4 the collected data are sorted by the size categories ("less than normal", "normal", "more than normal"), the meal type or time (breakfast, lunch, and dinner), and the day of the week (Sunday, Monday, etc.), as illustrated in FIGS. 14E-14K. The coefficient of variation is calculated by size category, meal type or time, and the day of the week. If none of the calculated coefficients exceeds CVmax the user interface is suitable for the user. In such a case the feed forward inputs to the graphical user interface would be, in the one dimensional case, a meal size value, a meal type or time value and a day of the week value for a pending meal. The feed forward feed forward information-to-insulin bolus information map of FIG. 9 may then, for example, include 21 maps that each map the user-selected feed forward input values of meal size to different corresponding insulin bolus information depending upon meal type or time, e.g., breakfast, lunch or dinner and also depending upon the day of the week, e.g., Sunday, Monday, etc. The corresponding insulin bolus information, in this case, may be, for example, an insulin bolus profile equal to the average bolus profile, by meal type or time and also by day of the week, for the user-specified categories of meal size using the information from the statistical analysis step 4 of FIGS. 14E and 14K.

In any or all of the foregoing steps, the type or time of meal, type of day, and/or day of the week may be determined automatically by the system 10, and therefore need not be manually entered into the graphical user interface by the patient. It will be appreciated that while the foregoing example used a coefficient of variation as a metric for the measure of inter-category pattern identification in the form of a spread of the bolus response, one or more other conventional metrics may be used in the statistical analysis conducted in accordance with steps 174-82 of FIG. 11.

In embodiments of a user interface where at least one of the axes represents a (pseudo-) continuous input, such as illustrated and described with respect to FIGS. 6 and 7, a model or series of models of the meal compensation bolus amount may be developed. Such a model or models would be a function of the various input variables, where one of the user-selected classifications is the location on the continuous axis of the user interface. If the model is sufficiently rigid, extrapolation may be used to assign a bolus amount recommendation in situations where the user chooses a value for the continuous input that falls outside of the range covered during the learning period.

Referring now to FIG. 12, a flowchart of one illustrative embodiment of the third process module of the process 150 is illustrated. If the third module of the process 150 is reached, the second process module of FIG. 11 was successful in determining a pattern in the patient-relevant information from which user-selected feed forward information could be mapped to corresponding insulin bolus information. The goal of the third process module is to reduce, where possible, the number of categories of user-selectable feed forward inputs. In the illustrated embodiment, the third process module of FIG. 12 accomplishes this goal by merging, where appropriate, adjacent categories of the user-selectable feed forward inputs. For example, it may be appropriate, as determined by the third process module of FIG. 12, to merge "normal" and "larger than normal" user-selectable input categories for a particular pattern into a single "normal" category.

The third process module begins at step 188 where a counter, K, is set to 1. Thereafter at step 190, the Kth pattern element of the pattern developed with the second process module of FIG. 11 is selected for processing. Thereafter at step 192, merging scenarios for the Kth pattern element are generated. As will be illustrated by example hereinafter, step 192 involves identifying every possible merging combination of the user-selectable feed forward inputs for the particular pattern element being processed. Following step 194, a statistical analysis of the patient-relevant information for each category merging scenario is conducted to identify whether any one or more of the categories may be merged. Thereafter at step 196, the "best" category merging scenario from the statistical analysis of step 194 is chosen based on one or more performance metrics. Following step 198, the categories for the Kth pattern element are merged according to the "best" category merging scenario identified at step 196. As used in this context, "best" is defined as the strategy, among competing strategies, that is selected by defining an appropriate cost function with appropriate weights, applying this cost function to all competing strategies, and selecting the strategy for which the cost is minimum. Additional constraints may also be defined which must be satisfied when solving for the best category merging scenario. Examples of such additional constraints include, but are not limited to, requiring uniform grid categories across all Kth elements of a grid pattern, requiring the merging of an entire category row or category column, and the like.

Following step 200, a determination is made as to whether steps 192-198 resulted in the changing, e.g., merging, of any of the categories of the Kth pattern element. If so, the process advances to step 202 where a determination is made as to whether the total number of categories of the Kth pattern element is now equal to a minimum desirable number, MIN, of categories, e.g., one or more. If not, the process 150 loops back to step 192. If it was determined at step 200 that none of the categories of the Kth pattern element changed, or at step 202 that the total number of categories is equal to the minimum number, MIN, of categories, the processing of the Kth pattern element is complete and the process 150 advances to step 204 where it is determined whether "K" is equal to the total number of pattern elements. If not, then all of the pattern elements have not yet been processed and the process 150 advances to step 206 where the value of "K" is incremented by one, and then loops back to step 190 to process the next pattern element. When all of the pattern elements have been processed, step 204 advances to step 208 where one or more maps, e.g., of the type illustrated in FIG. 9, are created that map the user-selectable feed forward input categories or category combinations to corresponding insulin delivery information. Thereafter at step 210 the process 150 stops, and the graphical user interface and one or more feed forward-to-insulin deliver information maps just created by the process 150 may be implemented in the system 10 and used as described hereinabove with respect to FIGS. 2-9 to recommend and/or administer insulin to a patient based on the user-selectable feed forward information provided to the interface by the patient.

The example patient-relevant information pattern developed in FIGS. 14A-14K will now be used as an example to illustrate operation of the third process module of FIG. 12. In this example, 21 one-dimensional pattern elements were developed, e.g., patterns of meal size only for each of the three meal types for each of the seven days of the week. The total number of pattern elements in this example is thus 21, and the outer loop defined by step 206 will accordingly be executed 20 times. The order of processing the 21 different pattern elements may be arbitrary, and in this example the $1^{st}$ pattern element (K=1) is Monday breakfast, followed by Monday lunch, Monday dinner, Tuesday breakfast, etc. The first execution of step 190 thus selects the Monday breakfast pattern element.

To facilitate the description of this third process module, the "less", "normal" and "more" feed forward input categories in the example illustrated in FIGS. 14A-14K are assigned numerical values, e.g., "less"=1, "normal"=2 and "more"=3. Designating a hyphen between categories as identifying merging categories, the three possible category merging scenarios resulting from step 192 are thus:

((1,1), (2,1), (3,1)),
(([1-2],1), (3,1)), and
((1,1),([2-3], 1)), which corresponds to ((less, normal, more), (less+normal, more), and (less, normal+more)) for Monday breakfast.

In one exemplary embodiment, the statistical analysis of each category merging scenario is conducted by incrementing the number of categories in the merging scenario in steps of two until complete sample distribution along the meal size axis is covered. It may be desirable to use categories of equal width, although this is not required. It is also desirable to center each of the categories on the median value of the sample distribution. Assessing the acceptability of each merging scenario may be accomplished in a number of different ways. In one exemplary embodiment, differences between the minimum and maximum values from the median values of each category are translated to incremental insulin bolus values. The incremental insulin bolus values are, in turn, are translated into expected deviations or percentiles from a post-meal blood glucose target. These deviations or percentiles may then be compared to one or more predetermined threshold levels to determine whether the category merging scenario is acceptable. In an alternate embodiment, a number of hypothetical samples may be drawn for a Monte Carlo simulation from the sample distribution within each category. Each sample's deviation from the category's median is then processed in the same way as just described in the previous embodiment.

The result of step 194 is the identification of all category merging scenarios that are acceptable based on the statistical analysis of each. Step 194 will always yield at least one scenario since the original scenario, e.g., no category merging, ((1,1), (2,1), (3,1)), is included in the analysis. If more than one scenario emerges from step 194, step 196 selects the "best" of the multiple scenarios resulting from step 194 based on one or more performance metrics. The one or more performance metrics may include, for example, but should not be limited to, one or any combination of data variance from the mean or median within each scenario, cost function associated with each scenario, desirability of having fewer overall categories, incremental advantage of reducing the number of categories by one, etc. Those skilled in the art will recognize other techniques for choosing the "best" of multiple category merging scenarios resulting from step 194, and such other techniques are contemplated by this disclosure.

At step 198, the feed forward input categories for Monday breakfast are merged according to the "best" merging scenario determined at step 196. One example result may be the second merging scenario illustrated above, which may be implemented by merging the "less" and "normal" categories into a "normal" category so that two categories of "normal" and "more" now remain. In any case, step 202 directs the process 150 back through steps 192-200 until the total number of categories does not change, and step 204 directs the process 150 back through steps 190-202 until all of the pattern elements, e.g., through Sunday dinner, are processed. The result of the third process module illustrated in FIG. 12, with the example one-dimensional data set of FIGS. 14A-14K, is that the user-selectable feed forward information presented to the patient for any meal on any day of the week may include one, two or three input categories.

In the foregoing example, the feed forward input categories were represented by one-dimensional information in the form of meal size, and the total number of input categories was three, e.g., "less", "normal" and "more." It should be understood that in embodiments of the graphical user interface that that include multiple-dimensional information, i.e., multiple axes of user-selectable feed forward information, the number of category merging scenarios increases significantly. The number of category merging scenarios likewise increases as the total number of user-selectable feed forward categories increases. For example, in embodiments of the graphical user interface that include two-dimensional information, e.g., a meal size axis and a meal speed axis, and that include four user-selectable categories of feed forward information along each axis, e.g., "small", "medium small", "medium large" and "large", and "slow", "medium slow", "medium fast" and "fast", the possible category merging scenarios are (if numbers 1-4 are assigned to the four input values on each axis):

((1,1), (1,2), (1,3), (1,4), (2,1), (2,2), (2,3), (2,4), (3,1), (3,2), (3,3), (3,4), (4,1), (4,2), (4,3), (4,4)), ((1,[1-2]), (1,3), (1,4), (2[1-2]), (2,3), (2,4), (3,[1-2]), (3,3), (3,4), (4,[1-2]), (4,3), (4,4)), ((1,1), (1,[2-3]), (1,4), (2,1), (2,[2-3]), (2,4), (3,1), (3,[2-3]), (3,4), (4,1), (4,[2-3]), (4,4)), ((1,1), (1,2), (1,[3-4]), (2,1), (2,2), (2,[3-4]), (3,1), (3,2), (3,[3-4]), (4,1), (4,2), (4,[3-4])), (([1-2],1), ([1-2],2), ([1-2],3), ([1-2],4), (3,1), (3,2), (3,3), (3,4), (4,1), (4,2), (4,3), (4,4)), ((1,1), (1,2), (1,3), (1,4), ([2-3],1), ([2-3],2), ([2-3],3), ([2-3],4), (4,1), (4,2), (4,3), (4,4)), and ((1,1), (1,2), (1,3), (1,4), (2,1), (2,2), (2,3), (2,4), ([3-4],1), ([3-4],2), ([3-4],3), ([3-4],4)).

In this case, two rows at a time may be merged to create the merged category sets.

The patient fine tunes the system 10 by interacting with it daily. It is desirable to use this daily interaction, which may be supplemented with additional patient and/or health care professional feedback, in a "learning" mode to create a patient-specific history of practiced therapy from which one or more patterns can be extracted for purposes of updating or refining the graphical user interface described herein. Learning in this context comprises monitoring patient interaction with the graphical user interface as well as monitoring patient and health care professional feedback, and adapting operation of the graphical user interface based on information resulting from such monitoring. For purposes of this document, learning excludes the initial exercise of collecting patient-relevant information and creating the graphical user interface from the collected information as described herein.

Therapies can change in practice for any of several reasons. For example, the patient may change his or her lifestyle such as revising or introducing daily exercise habits. As another example, the patient may consciously or unconsciously change his or her eating habits, such as by consuming smaller or larger quantities during meal and/or snack times. As a further example, the patient's short and/or long term body weight may change due to exercise, illness, consuming more or less food during meals, changes in body metabolism, etc.

Figure 15:
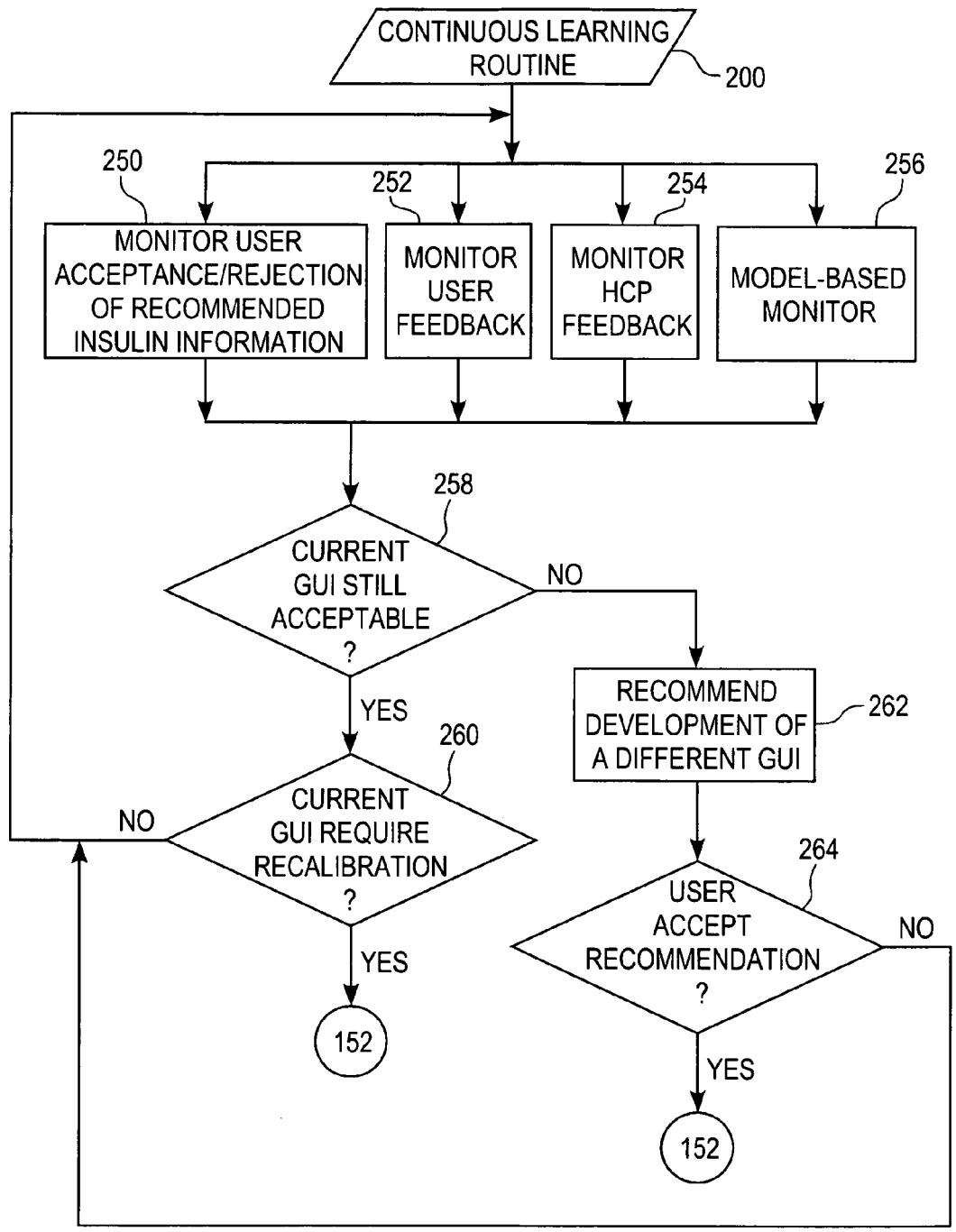
FIG. 15 is a flowchart of one illustrative embodiment of a continuous learning process.

Referring to FIG. 15, a flowchart of one illustrative embodiment of a continuous learning process 200 for a graphical user interface of the type illustrated and described herein is shown. The process 200 may be executed by the processor 14, may be conducted manually, or may be executed via a combination of manually conducted steps and steps executed by the processor 14. For purposes of this description, however, the process 200 will be described as being executed by the processor 14. The process 200 begins at steps 250, 252, 254 and 256 where the processor 14 is operable in a time-sharing operational mode, or where multiple processors are operable or code is executed sequentially, to monitor patient acceptance or rejection of insulin delivery recommendations produced by the system 10, in embodiments of the system 10 configured to make such recommendations, to monitor any feedback entered into the system 10 by the user, to monitor any feedback or other information entered into the system 10 by the health care professional and/or to monitor one or more model-based functions each responsive to measurement of one or more patient conditions to estimate another patient condition that is different from the one or more patient conditions. Any such monitoring may include storing information. Any such stored information may be evaluated immediately or in the future, and/or may be re-evaluated when new entries or updates are made to the database and/or to the one or more system control algorithms. Examples of user feedback entered into the system 10 include, but are not limited to, any of the information illustrated in FIG. 13, user inputs to the implemented GUI, and other user-related information such as exercise, stress and/or illness intensity or state, menstrual cycle information, results of one or more user-monitored physiological states, results of user-monitored glycemic control, such as by using HbA1C, and the like. Any such information may be entered into the system 10 via any of the mechanisms described hereinabove. Alternatively or additionally, the input device 18 and/or 36 may include a number of dedicated input buttons, keys or the like, which may be color-coded or otherwise readily identifiable, that allow the user to input usual and unusual behavior/conditions via readily recognizable input mechanisms. Examples of health care professional (HCP) feedback entered into the system 10 include, but are not limited to, results of tests performed by the health care professional, dietary, exercise and/or other lifestyle related advice or recommendations, results of one or more HCP-monitored physiological states, results of HCP-monitored glycemic control, such as by using HbA1C, and the like. Examples of model-based functions include, but are not limited to, model-based estimates of glucose absorption, insulin utilization or the like, based, at least in part, on blood glucose and/or HBA1C measurements.

In any case, the process 200 advances from steps 250-256 to step 258 where the processor 14 is operable to determine whether the currently implemented GUI is still acceptable. The processor 14 is operable to execute step 258 by processing the information that has been provided at steps 250-256 over time. For example, if the processor 14 determines that the user, over time, has consistently rejected/modified the insulin delivery information recommended by the system 10, the processor 14 may be operable to follow the "no" branch of step 258. Likewise, if the processor 14 determines from feedback information provided by the user, feedback information provided by the health care provider and/or model-based information that one or more operational features of the graphical user interface is/are inconsistent with the parameters used to establish and define the GUI, the processor 14 may be operable to follow the "no" branch of step 258. Other factors to consider and other techniques for determining whether the currently implemented GUI is acceptable will occur to those skilled in the art, and such other factors and/or techniques are contemplated by this disclosure.

If the processor 14 determines at step 258 that the currently implemented GUI is still acceptable, execution of the process 200 advances to step 260 where the processor 14 is operable to determine whether the currently implemented GUI requires any recalibration. Generally, one or more of the same considerations used at step 258 may be used by the processor 14 at step 260 to make such a determination. If the processor 14 determines that the currently implemented GUI does not require recalibration, execution of the process 242 loops back to execute steps 250-256. If, on the other hand, the processor 14 determines at step 260 that the currently implemented GUI requires recalibration, execution of the process 200 jumps to step 152 of the process 150 illustrated and described with respect to FIGS. 10-12. There, the map correlating user-selectable feed forward inputs to the currently implemented GUI to corresponding insulin delivery information can be modified by the processor 14 in accordance with the patient-specific history collected during the repeated execution of the process 200.

If the processor 14 determines at step 258 that the currently implemented GUI is no longer acceptable, execution of the process 200 advances to step 262 where the processor 14 controls the display unit 20 and/or 38 to display a message recommending development of a different GUI. From step 262, execution of the process 200 advances to step 264 where the processor 14 is operable to prompt the user for a response to the recommendation displayed at step 262. If the user chooses not to accept the recommendation, execution of the process 200 loops back to steps 250-256. If, on the other hand, the user chooses at step 264 to accept the recommendation displayed at step 262, execution of the process 200 jumps to step 152 of the process 150 illustrated and described herein with respect to FIGS. 10-12. There, the processor 14, user and/or health care professional may select a different GUI or may determine that none of the GUI choices are suitable for use with the patient.

The learning process 200 uses the entered information to create patient history from which a pattern of patient's therapy is extracted. In embodiments where the process 200 is executed by the processor 14, the processor 14 may be configured to run the process 200 in the background during otherwise normal operation of the system 10. The process 200 may also be designed to be executed synchronously with the otherwise normal operation of the system 10.

The learning process 150 may be protocol driven to maintain appropriate variability that is suitable to capturing pattern information. Alternatively or additionally, the interaction may be done free style where day to day activities will be entered along with the therapy. The length of the learning interaction may be designed to be some fixed number of days. Alternatively or additionally, convergence criteria may be implemented to identify an end of a particular learning period, such as statistical distribution parameters not changing more than certain threshold value.

The learning process 150 may illustratively be implemented as a module that works with other therapy advice supporting applications. In such cases, the learning process 150 may be used to map user's subjective input to a standardized and quantified therapy such as insulin amount. Once quantified and standardized, the advice information or commanding advice information may be relayed to or integrated with inputs for a $3^{rd}$ party advice supporting application. The learning process 150 may thus be used to directly provide a therapy, or to supply information that may be used by a $3^{rd}$ party advice supporting application for, e.g., communicating infusion information to an attached infusion pump.

Quantifying meals is at times difficult for the patient. However, the quality of the inputs to the learning process 150 is the burden of the patient and/or health care professional. The qualification of data acceptability in the learning process 150 is thus based on implicit understanding that the data record provided to the learning process 150 represents quality information that contains either new content or additional useful information.

In some embodiments, the patient will provide the event and will also administer the therapy. Since the patient may or may not administer the therapy that is recommended by the system 10, the patient is in such cases training the system 10 on how he/she maps the therapy. Changes or modifications to the therapy are expected to be done directly by the patient by overriding the recommended therapy. The learning process 200 thus provides statistical distribution content of the overall information collected.

The statistical part of the collected data may be analyzed to provide monitoring information. The data analysis may illustratively be broken into two data sets: (1) data set dominated with old data and (2) data set dominated with recent data set. The old data set is representative of the data distribution when therapy was last reset. The recent data set considers data around the current time window with a time frame for example of about a month or so. The two sets of data distributions may then be contrasted, and changes found between the two distributions are generally indicative of changes in the patient's lifestyle and/or progressive changes in therapy related parameters. This can trigger different alternatives to revise the mapping or the therapy. This analysis may be triggered when any new data record received, and/or after a batch of new data records are received. The need for changes in therapy is based on monitoring statistical properties between original records set and the newer data records.

Regular revision by the patient of the insulin information recommended by the system 10 is generally an indication of (1) insufficient or inadequate learning by system 10, and/or (2) the inability of the original therapy to meet the current therapy needs. This, for example, may happen when the patient has experienced a lifestyle change, which now causes the therapy information recommended by the system 10 to be insufficient or incorrect. The frequency of occurrence of patient overrides can thus be used as a trigger for revising the mapping or the therapy.

The therapy monitoring may be enhanced if glucose measurements are available to the system. Infrequent measurements may be enhanced with use of a patient model which may be used to monitor and predict blood glucose levels. The action of therapy is included in the patient model. Such a patient model may be individualized to the particular patient, or be an appropriate population representative model describing the behavior of the patient. The glucose measurements or predicted glucose measurements provide a monitoring module that can indicate that the current therapy is deviating and needs further specific data to improve therapy.

The therapy is typically evaluated by the patient by examining deviations from the recommended therapy. If the recommended therapy is modified (overridden) regularly, this indicates a change in patient behavior and the GUI should be revised. The statistical description is continuously measured. It can be used to monitor changes when the therapy and/or meal input distribution changes. Glucose measurement and other indicators of good glucose control such as HBA1C provide a check on the effectiveness of the therapy.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. A system for determining drug administration information for a user based at least on the user ingesting a meal, the system comprising:
   an input device providing for user input of feed forward information in the form of meal information having a first parameter component corresponding to carbohydrate content of the meal and a second parameter component corresponding to an expected speed of overall glucose absorption from the meal by the user, wherein the meal information relates to a meal that is to be ingested in the future,
   a data storage device having stored therein a map correlating values of the first and second parameter components to drug administration information, and
   a processor responsive to the user input of the feed forward information to determine corresponding drug administration information according to the map,
   wherein the input device includes a display unit, and wherein the processor controls the display unit to display a graphical user interface,
   wherein the graphical user interface has a first axis defined by values of the first parameter component and a second axis defined by values of the second parameter component, the graphical user interface providing for the user input of feed forward information in the form of a user selection of a corresponding pair of values of the first and second parameter components; and
   wherein the input device and the processor provide the user with the ability to modify one or more of time and date stamp information that is associated with previously entered meal information subsequent to actual meal ingestion.

2. The system according to claim 1 wherein the graphical user interface includes a touch responsive interface and defines a grid-type user interface providing for the user selection of a corresponding pair of values of the first and second parameter components.

3. The system according to claim 1 wherein the graphical user interface defines a continuous function of the first and second parameter components.

4. The system according to claim 1 wherein the drug administration information relates to a blood glucose lowering drug or insulin.

5. The system according to claim 1 wherein the processor controls the display unit to display via the graphical user interface values of the carbohydrate content in a format selected from direct estimates of carbohydrate weight, meal size values, and meal size values relative to a reference meal size.

6. The system according to claim 1 wherein the processor controls the display unit to display via the graphical user interface values of the expected speed in a format selected from meal duration values, meal duration values relative to a reference meal duration, and total glycemic index values.

7. The system according to claim 1 wherein the processor controls the display unit to display via the graphical user interface values of the expected speed in a format comprising a fat amount, a protein amount, and a carbohydrate amount, and displays the values of the carbohydrate content in a format comprising meal size values for each of the fat amount, protein amount and carbohydrate amount.

8. The system according to claim 1 wherein the graphical user interface provides for the user input of feed forward information in a format comprising a user selection of a meal size value in terms of fat amount, a meal size in terms of protein amount, and a meal size in terms of carbohydrate amount and wherein the processor controls the display unit to display via the graphical user interface the meal size values in the form of fat amount, protein amount and carbohydrate amount relative to reference meal size values in terms of fat, protein and carbohydrate amounts respectively.

9. The system according to claim 1 wherein the input device provides for user input of additional feed forward information comprising at least one of exercise information, user stress information, user illness information, and user menstrual cycle information,
   wherein the data storage device has stored therein an additional map correlating the at least one of the exercise information, the user stress information, the user illness information, and the user menstrual cycle information to modification information, and
   wherein the processor is responsive to user input of the at least one of the exercise information, the user stress information, the user illness information, and the user menstrual cycle information to modify the corresponding drug administration information according to the modification information determined via the additional map.

10. The system according to claim 1 wherein the processor is operable to determine whether a complete user input to the graphical user interface has been detected, and wherein the processor is operable to time and date stamp the graphical user interface input and to enter the date and time stamped graphical user interface input into a database contained within the data storage device if the processor detects that a complete user input to the graphical user interface has occurred.

11. The system according to claim 1 wherein the system provides the user with the ability to append new or more accurate information onto the previously entered meal information.

12. The system according to claim 1 wherein the processor controls the display unit to display via the graphical user interface at least some of the corresponding drug administration information.

13. The system according to claim 12 wherein the processor monitors occurrences of user acceptance and rejection of the displayed corresponding drug administration information determined according to the map, and determines whether the system is acceptable for use by the user based at least in part on the occurrences of user acceptance and rejection of the corresponding drug administration information.

14. The system of claim 13 wherein, if the processor determines that the system is acceptable for use by the user, then the processor determines whether the system requires recalibration based at least in part on the occurrences of user acceptance and rejection of the drug administration information.

15. The system of claim 1 further comprising means for providing for input of user feedback information, and wherein the processor monitors the user feedback information and determines whether the system is acceptable for use by the user based at least in part on the user feedback information.

16. The system of claim 15 wherein, if the processor determines that the system is acceptable for use by the user, then the processor determines whether the system requires recalibration based at least in part on the user feedback information.

17. The system of claim 1 further comprising means for providing for input of health care professional feedback information, and wherein the processor monitors the health care professional feedback information and determines whether the system is acceptable for use by the user based at least in part on the health care professional feedback information.

18. The system of claim 17 wherein, if the processor determines that the system is acceptable for use by the user, then the processor determines whether the system requires recalibration based at least in part on the health care professional feedback information.

19. The system of claim 1 further comprising at least one model-based function responsive to measurement of one or more user conditions to estimate another user condition different than the one or more user conditions, and wherein the processor monitors the at least one model-based function and determines whether the system is acceptable for use by the user based at least in part on the at least one model-based function.

20. The system of claim 19 wherein, if the processor determines that the system is acceptable for use by the user, then the processor determines whether the system requires recalibration based at least in part on the at least one model-based function.

\* \* \* \* \*

UNITED STATES PATENT AND TRADEMARK OFFICE
CERTIFICATE OF CORRECTION

PATENT NO. : 7,941,200 B2
APPLICATION NO. : 11/297733
DATED : May 10, 2011
INVENTOR(S) : Stefan Weinert et al.

Page 1 of 1

It is certified that error appears in the above-identified patent and that said Letters Patent is hereby corrected as shown below:

Title Page, Item 75, "Stefhan Weinert" should read --Stefan Weinert--

Col. 5, Line 67, "to determined whether" should read --to determine whether--

Col. 8, Line 51, "according one embodiment" should read --according to one embodiment--

Col. 9, Line 21, "may alternatively formed of" should read --may be alternatively formed of--

Col. 19, Line 39, "user input the GUI" should read --user input to the GUI--

Col. 31, Line 11, insert --)-- after "etc."

Col. 32, Line 50, delete the words "feed forward" at the beginning of the line

Col. 33, Line 4, "steps 174-82" should read --steps 174-182--

Col. 34, Line 63, delete the word "are"

Col. 35, Line 45, delete the word "that"

Col. 38, Line 64, "data record received" should read --data record is received--

Signed and Sealed this
Fourteenth Day of February, 2012

David J. Kappos
*Director of the United States Patent and Trademark Office*